(12) United States Patent
Ahmed et al.

(10) Patent No.: US 8,323,679 B2
(45) Date of Patent: *Dec. 4, 2012

(54) FLEXIBLE, COMPRESSED INTRAVAGINAL RINGS, METHODS OF MAKING AND USING THE SAME, AND APPARATUS FOR MAKING THE SAME

(75) Inventors: Salah U. Ahmed, New City, NY (US); Tahseen A. Chowdhury, Washington Township, NJ (US); Yi Luo, Harriman, NY (US)

(73) Assignee: TEVA Women's Health, Inc., Woodcliff Lake, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/984,729

(22) Filed: Jan. 5, 2011

(65) Prior Publication Data

US 2011/0212155 A1 Sep. 1, 2011

Related U.S. Application Data

(62) Division of application No. 11/725,563, filed on Mar. 20, 2007, now Pat. No. 7,910,126.

(60) Provisional application No. 60/783,411, filed on Mar. 20, 2006.

(51) Int. Cl.
| | | |
|---|---|---|
| *A61F 6/14* | (2006.01) | |
| *A61K 38/43* | (2006.01) | |
| *A61P 15/02* | (2006.01) | |
| *A61P 29/00* | (2006.01) | |
| *A61P 31/00* | (2006.01) | |
| *A61P 23/02* | (2006.01) | |
| *A61P 19/10* | (2006.01) | |
| *B29C 3/52* | (2006.01) | |

(52) U.S. Cl. .... 424/432; 514/9.7; 424/94.1; 264/331.18
(58) Field of Classification Search .......... None
See application file for complete search history.

(56) References Cited

U.S. PATENT DOCUMENTS

| | | |
|---|---|---|
| 3,545,439 A | 12/1970 | Duncan |
| 3,920,805 A | 11/1975 | Roseman |
| 3,995,633 A | 12/1976 | Gougeon |
| 4,094,685 A | 6/1978 | Lester et al. |
| 4,235,236 A | 11/1980 | Theeuwes |
| 4,249,531 A | 2/1981 | Heller et al. |
| 4,286,587 A | 9/1981 | Wong |
| 4,311,543 A | 1/1982 | Strickman et al. |
| 4,553,972 A | 11/1985 | Vickery |
| 4,591,496 A | 5/1986 | Cohen et al. |
| 4,607,630 A | 8/1986 | Spits |
| 4,823,814 A | 4/1989 | Drogendijk et al. |
| 5,036,867 A | 8/1991 | Biswas |
| 5,047,244 A | 9/1991 | Sanvordeker et al. |
| 5,378,416 A | 1/1995 | Kishi et al. |
| 5,672,313 A | 9/1997 | Shiga et al. |
| 5,894,842 A | 4/1999 | Rabin et al. |
| 6,131,575 A | 10/2000 | Lenker et al. |
| 6,143,367 A | 11/2000 | Bartol et al. |
| 6,216,698 B1 | 4/2001 | Regula |
| 6,264,638 B1 | 7/2001 | Contente |
| 6,319,520 B1 | 11/2001 | Wuthrich et al. |
| 6,645,137 B2 | 11/2003 | Ulmsten et al. |
| 6,652,874 B2 | 11/2003 | Ragavan et al. |
| 2004/0044080 A1 | 3/2004 | Place et al. |
| 2004/0220333 A1 | 11/2004 | Tadros et al. |

OTHER PUBLICATIONS

Martin, A. et al., "20. Polymer Science," in *Physical Pharmacy. Physical Chemical Principles in the Pharmaceutical Sciences*, 4$^{th}$ Ed., Mundorff, G.H. and Wilson, D., eds., Lea & Febiger. Malvern. Pennsylvania, pp. 575-578 (1993).

International Search Report and Written Opinion for International Patent Application No. PCT/US07/06850, mailed Dec. 14, 2007, United States Patent and Trademark Office.

Office Action, U.S. Appl. No. 11/725,563, mailed on Oct. 27, 2009, United States Patent and Trademark Office, Alexandria, Virginia.

Reply Under 37 C.F.R. § 1.111, U.S. Appl. No. 11/725,563, submitted Jan. 27, 2010, to the United States Patent and Trademark Office, Alexandria, Virginia.

Interview Summary, U.S. Appl. No. 11/725,563, mailed Jul. 20, 2010, United States Patent and Trademark Office, Alexandria, Virginia.

Notice of Allowance and Interview Summary, U.S. Appl. No. 11/725,563, mailed Jul. 28, 2010, United States Patent and Trademark Office, Alexandria, Virginia.

Notice of Allowance and Interview Summary, U.S. Appl. No. 11/725,563, mailed Oct. 6, 2010, United States Patent and Trademark Office, Alexandria, Virginia.

*Primary Examiner* — Robert A Wax
*Assistant Examiner* — Danah Al-Awadi
(74) *Attorney, Agent, or Firm* — Fanelli Haag & Kilger PLLC

(57) ABSTRACT

The present invention is directed to flexible, compressed intravaginal rings comprising a substantially homogeneous compressed mixture comprising a polymethacrylate, a plasticizer, and an active agent, and methods of making and using the same, and apparatus for making the same.

29 Claims, 10 Drawing Sheets

FLEXIBLE, COMPRESSED INTRAVAGINAL RINGS, METHODS OF MAKING AND USING THE SAME, AND APPARATUS FOR MAKING THE SAME

This application is a divisional application of U.S. patent application Ser. No. 11/725,563, filed Mar. 20, 2007, now U.S. Pat. No 7,910,126, which claims the benefit of the filing date of U.S. Appl. No. 60/783,411 filed Mar. 20, 2006, the entirety of which is fully incorporated by reference herein.

BACKGROUND OF THE INVENTION

1. Field of the Invention

The present invention is directed to flexible, compressed intravaginal rings comprising a substantially homogeneous compressed mixture comprising a polymethacrylate, a plasticizer, a thickener, and an active agent, and a method of using the same. The present invention is also directed to a method of making and an apparatus for making flexible, compressed intravaginal rings utilizing a compression tooling apparatus.

2. Background Art

Intravaginal drug delivery is an increasingly utilized method of drug administration. Intravaginal dosage forms can provide good adsorption of active agents as well as a means to avoid the first-pass effect in the liver. As a result, intravaginal delivery is an efficacious method for administering many types of active agents. Intravaginally administered active agents can be targeted for direct diffusion through the vaginal tissues to provide a local effect, or can be absorbed through the mucosa the vaginal tract, for example, to provide a systemic effect. Further, there are numerous conditions within and outside the vaginal and/or urogenital tract, such as hormonal dysfunctions, inflammation, infection, pain, and incontinence, that can be treated by intravaginal administration of pharmaceutically active agents.

Of the several methods of intravaginal drug delivery in the art, such as for example, the use of intravaginal rings, intrauterine devices, and intravaginal pessaries (see e.g., U.S. Pat. Nos. 4,823,814; 4,607,630; 4,553,972; 4,286,587; and 4,249,531), intravaginal rings provide a versatile, comfortable method to deliver active agents via the intravaginal route.

However, there is a need in the art for improved intravaginal rings capable of maintaining active agents in the vaginal and/or urogenital tract for extended periods of time to allow for maximum and uniform absorption of the active agent at the desired location within the vaginal and/or urogenital tract.

There is also a need in the art for a method and apparatus for making the flexible, compressed intravaginal rings of the present invention. It is generally known to make ring-shaped objects through molding or compression. Compression tooling apparatus exist for making ring-shaped tablets on a small scale size (see e.g., U.S. Pat. No. 5,672,313), but there exists a need for a compression tooling apparatus that can make a flexible, compressed ring-shaped object that is the size of an intravaginal ring.

BRIEF SUMMARY OF THE INVENTION

The present invention is directed to a flexible, compressed intravaginal ring comprising a substantially homogeneous compressed mixture comprising a polymethacrylate, a plasticizer, a thickener, and an active agent, wherein the thickener is present in a concentration of about 2% to about 20% by weight of the flexible, compressed intravaginal ring.

The present invention is also directed to a therapeutic kit comprising the flexible, compressed intravaginal ring of the present invention, and instructions for administering the flexible, compressed intravaginal ring to a female subject.

The present invention is also directed to a method of providing an active agent to a subject, the method comprising vaginally administering a flexible, compressed intravaginal ring to the subject, wherein the flexible, compressed intravaginal ring comprises a substantially homogeneous compressed mixture comprising a polymethacrylate, a plasticizer, a thickener, and an active agent.

The present invention is also directed to a process for preparing a flexible, compressed intravaginal ring, the process comprising:

mixing a polymethacrylate having a glass transition temperature, a plasticizer, a thickener, and an active agent at a temperature above the glass transition temperature of the polymethacrylate to form a substantially homogeneous mixture; and compressing the substantially homogeneous mixture at a temperature below the glass transition temperature of the mixture to form a flexible, compressed intravaginal ring.

The present invention is also directed to a product prepared by the process of the present invention.

In some embodiments, the process of the present invention further comprises cooling the substantially homogeneous mixture to a temperature below the glass transition temperature of the mixture.

In some embodiments, the process of the present invention further comprises curing the flexible, compressed intravaginal ring.

In some embodiments, the curing comprises heating the flexible, compressed intravaginal ring to a temperature above the glass transition temperature of the mixture.

In the process of the present invention, the compressing can comprise:

providing a compression tooling apparatus comprising a die, an upper punch, a lower punch and a core rod;

discharging the substantially homogeneous mixture into the die;

compressing the mixture between the upper punch and the lower punch to form the flexible, compressed intravaginal ring;

separating the upper and lower punches after compressing; and ejecting the flexible, compressed intravaginal ring from the die.

In some embodiments, the lower punch has a cylindrical bore and the core rod is inserted in the cylindrical bore and adjusted to a desired position. In some embodiments, the cylindrical bore and the core rod have threads for adjusting the core rod to a desired position. In some embodiments, the upper punch has a cavity and during the compression the core rod enters into the cavity of the upper punch. In some embodiments, the die has a cavity and a diameter of the cavity controls a size of an outer diameter of the flexible, compressed intravaginal ring. In some embodiments, the core rod has a diameter and the diameter of the core rod controls a size of an inner diameter of the flexible, compressed intravaginal ring.

In some embodiments, the polymethacrylate has a glass transition temperature of about 10° C. to about 50° C. Polymethacrylates suitable for use with the present invention include, but are not limited to, poly(n-butyl) methacrylate, poly(isopropyl) methacrylate, poly(ethyl) methacrylate, poly (butyl) methacrylate, poly(propyl) methacrylate, poly(hexyl) methacrylate, and combinations thereof.

Plasticizers suitable for use with the present invention include, but are not limited to, dibutyl sebacate, triethyl citrate, castor oil, triacetin, propylene glycol, polyethylene glycol, hydrogenated vegetable oil, cetyl alcohol, cetylstearyl alcohol, fatty acids, glycerides and triglycerides, polyoxyethylene glycols, butyl lactate, ethyl glycolate, ethyl lactate, sorbitol lactate, 1,2-butylene glycol, block polymers, and combinations thereof.

In some embodiments, the polymethacrylate and the plasticizer are present in a ratio of about 1:1 to about 9:1 by weight. In some embodiments, the polymethacrylate and the plasticizer are present in a ratio of about 2:1 to about 7:1 by weight. In some embodiments, the polymethacrylate and the plasticizer are present in a ratio of about 3:1 to about 6:1 by weight. In some embodiments, the polymethacrylate and the plasticizer are present in a ratio of about 3:1 to about 5:1 by weight. In some embodiments, the polymethacrylate and the plasticizer are present in a ratio of about 4:1 by weight.

Thickeners suitable for use with the present invention include, but are not limited to, fumed silica, colloidal silica, calcium silicate, gelatinized starch, microcrystalline cellulose, talc, magnesium stearate, and combinations thereof.

Active agents suitable for use with the present invention include, but are not limited to, a prostaglandin, a urinary incontinence agent, an analgesic, an anti-inflammatory agent, a hormonal agent, an anti-microbial, an anesthetic, an anti-osteoporosis agent, a peptide hormone, an enzyme, and combinations thereof.

In some embodiments, the flexible, compressed intravaginal ring of the present invention further comprises a pharmaceutically acceptable excipient selected from the group consisting of: a diluent, a binder, a lubricant, an antioxidant, and combinations thereof.

BRIEF DESCRIPTION OF THE DRAWINGS

FIG. 1A is a "top view. " FIG. 1B is a "side view."

FIG. 2 is a view of an upper punch.

FIG. 3 is a view of a lower punch.

FIG. 4 is a view of a core rod.

FIG. 5 is a view of a die.

FIG. 6 is a schematic representation of an ejector die.

DETAILED DESCRIPTION OF THE INVENTION

Figure 1A:
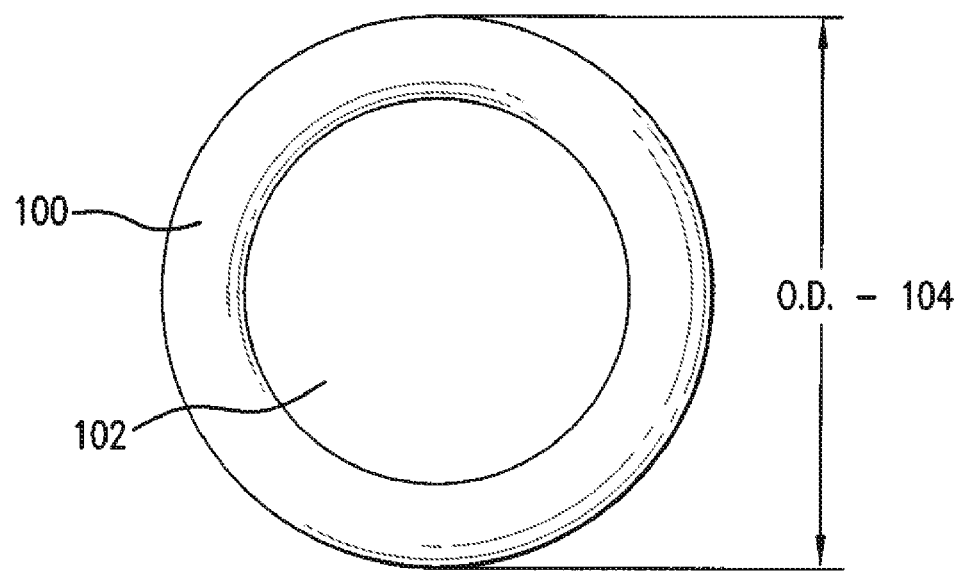
FIGS. 1A and 1B provide views of a flexible, compressed intravaginal ring of the present invention.

Throughout the present disclosure, all expressions of percentage, ratio, corporation, and the like are "by weight" unless otherwise indicated. As used herein, "by weight" is synonymous with the term "by mass," and indicates that a ratio or percentage defined herein is done according to weight rather than volume, thickness, or some other measure.

As used herein, the term "about," when used in conjunction with a percentage or other numerical amount, means plus or minus 10% of that percentage or other numerical amount. For example, the term "about 80%," would encompass 80% plus or minus 8%.

Pharmaceutical Compositions

The present invention is directed to a flexible, compressed intravaginal ring comprising a substantially homogeneous compressed mixture comprising a polymethacrylate, a plasticizer, a thickener, and an active agent.

An "intravaginal ring" is intended to encompass circular or toroidal shaped objects that provide for administration or application of an active agent to the vaginal and/or urogenital tract, including, e.g., the vagina, cervix, or uterus, of a female. An intravaginal ring of the present invention can be compressed into any variety of structures, including a toroid, suitable for insertion into or around the vagina, cervix, or uterus of a female.

"Homogeneous" refers to a composition, e.g., the flexible, compressed intravaginal ring, that has a substantially uniform distribution of ingredients throughout (i.e., a flexible, compressed intravaginal ring of the present invention does not have a composition gradient, or a multi-laminate structure).

A "mixture" refers to a composition comprising two or more ingredients. Thus, a "homogeneous mixture" refers to a composition of two or more ingredients, in which the ingredients are substantially uniformly distributed. For example, a "homogeneous mixture of a polymethacrylate, a plasticizer, a thickener, and an active agent" refers to the polymethacrylate, plasticizer, thickener, and active agent being substantially uniformly distributed throughout the mixture (i.e., there are no segments, regions, or areas of the mixture with substantially differing amounts of any of the ingredients).

In some embodiments, a substantially homogeneous mixture can comprise a "composite material." As used herein, a "composite" refers to a material in which the ingredients do not dissolve or merge completely, but which forms a substantially homogeneous material (i.e., a material without laminate structure or a composition gradient), whose macroscale structure (i.e., structure on the scale of about 1 mm or greater) maximizes specific performance properties (e.g., plasticity, modulus, glass transition temperature, etc.)

"Compressed" refers to a mixture that has been compacted or fused under pressure. A compressed mixture has a density that is greater than the mixture prior to compression. A compressed mixture can have a different shape than the mixture prior to compression. In some embodiments, a compressed mixture can have a structure that is elastically deformable. In some embodiments, compressing a substantially homogeneous mixture to form a compressed mixture can be achieved by compression molding, or alternatively, by the use of a die press.

The compressed intravaginal rings of the present invention are flexible. "Flexible" refers to the ability to bend easily, or the ability of a solid to withstand stress and strain without being damaged or broken. Stress is the force applied per unit area of a cross-section that causes deformation. The effect of stress is deformation or strain. Strain is the elongation or increase in the length in the solid relative to its original length. Thus, a measurement of the percentage of elongation that a solid is capable of prior to breaking is indicative of the flexibility of the solid. The greater the percentage of elongation of a solid, the more flexible the solid is. The measurement of mechanical properties in a solid is disclosed, for example, in "Polymer Science", *Chapter* 20, *Physical Pharmacy*, $4^{th}$ ed., Martin, Alfred, et al., eds., pp. 575-578 (1993).

The % elongation (% strain) of the flexible, compressed intravaginal ring can be examined by using, e.g., a Dynamic Mechanical Analyzer (DMA) Q 800 (TA Instruments, New Castle, Del.) or Instron 5542 (Wilson/Shore Instruments, Canton, Mass.). The strain-time curves and % elongation can be obtained under simple low stress and displacement time. The effect of stress is deformation or strain. Strain in tension is called elongation. Elongation (%)=[(L−L$_0$)/L$_0$]×100, in which L is the length under a given tensile stress and L$_0$ is the original length of the flexible solid dosage form.

In some embodiments, the percentage of elongation of a flexible, compressed intravaginal ring according to the present invention under a stress of about 1 millipascal (mPa) for about 1 minute can be, but is not limited to, about 10% to about 200%, about 30% to about 170%, about 40% to about 150%, about 50% to about 125%, or about 100% to about 120%. The percentage of elongation of a flexible, compressed intravaginal ring according to the present invention under a stress of about 0.5 mPa for about 5 minutes can be, but is not limited to, about 10% to about 200%, about 30% to about 170%, about 40% to about 150%, about 50% to about 125%, or about 90% to about 100%. The percentage of elongation of a flexible, compressed intravaginal ring according to the present invention under a stress of about 0.5 mPa for about 2 minutes can be, but is not limited to, about 10% to about 200%, about 30% to about 170%, about 40% to about 150%, about 50% to about 125%, or about 70% to about 80%. The percentage of elongation of a flexible, compressed intravaginal ring according to the present invention under a stress of about 0.75 mPa for about 1 minute can be, but is not limited to, about 10% to about 200%, about 30% to about 170%, about 40% to about 150%, about 50% to about 125%, or about 70% to about 80%. The percentage of elongation of a flexible, compressed intravaginal ring according to the present invention under a stress of about 0.5 mPa for about 1 minute can be, but is not limited to, about 10% to about 200%, about 25% to about 170%, about 30% to about 150%, about 40% to about 100%, or about 60% to about 70%.

In some embodiments, the flexible, compressed intravaginal rings are also elastic. For example, a flexible, compressed intravaginal ring of the present invention can be deformed or flexed easily, such as, for example, using finger pressure (e.g., applying pressure from opposite external sides of the ring using the fingers), and upon removal of the pressure, return to its original shape. The flexible properties of the intravaginal ring of the present invention are particularly important and useful for enhancing user comfort while using the intravaginal ring, and ease of administration and removal of the ring.

The present invention relates to flexible, compressed compositions comprising a polymethacrylate. A "polymethacrylate" is a polymer having the following structure, I:

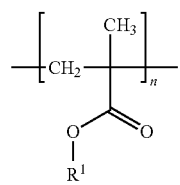

wherein n≧2, and R$^1$ is an alkyl substituent. In some embodiments, n is from 100 to about 3000, 200 to about 2500, or 300 to about 200. In some embodiments, n is from 500 to about 2000, 1000 to about 2000, or 1500 to about 2000. Polymethacrylates suitable for use with the present invention include, but are not limited to, those in which R$^1$ is a C$_2$-C$_{18}$ straight chain, branched, or cyclic alkyl group, or in some embodiments R$^1$ is a C$_2$-C$_{12}$ straight chain, branched, or cyclic alkyl group. In some embodiments, R$^1$ is a C$_2$-C$_6$ straight chain, branched, or cyclic alkyl group.

Straight chain and branched polymethacrylates for use with the present invention include, but are not limited to, poly(ethyl) methacrylate, poly(isopropyl) methacrylate, poly(propyl) methacrylate, poly(butyl) methacrylate, poly(n-butyl) methacrylate, poly(hexyl) methacrylate, poly(n-hexyl) methacrylate, poly(n-heptyl) methacrylate, poly(ethylhexyl) methacrylate, poly(n-decyl) methacrylate, poly(isodecyl) methacrylate, poly(lauric) methacrylate, poly(stearic) methacrylate, and combinations thereof.

Examples of cyclic alkyl polymethacrylates include, but are not limited to, poly(cyclohexyl) methacrylate, poly(benzyl) methacrylate, poly(iso-bornyl) methacrylate, poly(adamantyl) methacrylate, poly(dicyclopentenyloxyethyl) methacrylate, poly(dicyclopentenyl)methacrylate, poly(dicyclopentenylacrylate, 3,3,5-trimethylcyclohexylmethacrylate, 4-tert-butylcyclohexylmethacrylate, and combinations thereof.

In some embodiments, a crosslinking agent can be used. Useful crosslinking agents include: ethyleneglycol dimethacrylate, 1,4-butanediol dimethacrylate, 1,3-butanediol dimethacrylate, triethyleneglycol dimethacrylate, tetraethyleneglycol dimethacrylate, polyethyleneglycol-400 dimethacrylate, neopentylglycol dimethacrylate, bisphenol A dimethacrylate, ethoxylated bisphenol A dimethacrylate, trimethylolpropane trimethacrylate, tripropyleneglycol acrylate, and combinations thereof.

In addition, one of skill in the art will recognize that other polymethacrylates can be used in the present invention including those listed in the *Handbook of Pharmaceutical Excipients*, Pharmaceutical Press 4th Ed. (2003), which is incorporated herein by reference in its entirety. While not being bound by a particular theory, in some embodiments the polymethacrylate is biocompatible. The term "biocompatible" refers to the capability of coexistence of the polymethacrylate with living tissues without causing harm.

In some embodiments, a flexible, compressed intravaginal ring of the present invention comprises a polymethacrylate in concentration of about 5% to about 95%, by weight, of the flexible, compressed intravaginal ring. In some embodiments, a flexible, compressed intravaginal ring of the present invention comprises a polymethacrylate in concentration of about 25% to about 95%, by weight, or alternatively about 50% to about 90%, by weight, of the flexible, compressed intravaginal ring. In some embodiments, a flexible, compressed intravaginal ring of the present invention comprises a polymethacrylate in concentration of about 60% to about 85%, by weight, or alternatively about 75%, by weight, of the flexible, compressed intravaginal ring.

A "plasticizer" is a substance that can be added to a polymer or a mixture thereof to enhance its softness and/or pliability. Plasticizers suitable for use with the present invention include, but are not limited to, dibutyl sebacate, triethyl citrate, castor oil, triacetin, propylene glycol, polyethylene glycol, hydrogenated vegetable oil (e.g., LUBRITAB®, Penwest Pharmaceuticals Co., Patterson, N.J.), cetyl alcohol, cetylstearyl alcohol, fatty acids, glycerides and triglycerides, polyoxyethylene glycols, butyl lactate, ethyl glycolate, ethyl lactate, sorbitol lactate, 1,2-butylene glycol, block copolymers, and mixtures thereof.

In some embodiments, a flexible, compressed intravaginal ring of the present invention comprises a plasticizer in a concentration of about 1% to about 50%, by weight, of the flexible, compressed intravaginal ring. In some embodiments, a flexible, compressed intravaginal ring of the present invention comprises a plasticizer in a concentration of about 5% to about 40%, by weight, or alternatively about 10% to about 30%, by weight, of the flexible, compressed intravaginal ring. In some embodiments, a flexible, compressed intravaginal ring of the present invention comprises a plasticizer in a concentration of about 15% to about 20%, by weight, of the flexible, compressed intravaginal ring.

In some embodiments of the present invention, the polymethacrylate, mixture of polymethacrylates, or mixture of a polymethacrylate and a plasticizer can be selected based on the glass transition temperature of the polymethacrylate, mixture of polymethacrylates, or mixture of a polymethacrylate and a plasticizer. A "glass transition temperature" or "$T_g$" refers to the temperature at which a polymer, e.g., a polymethacrylate, is transformed from a hard glass-like state to a soft rubber-like state. Polymethacrylates with a wide range of $T_g$ temperatures can be used in the present invention. In some embodiments, the $T_g$ can be a parameter useful for selecting a polymethacrylate, or a mixture thereof, for use in the present invention. For example, the $T_g$ of the homogeneous mixture can be controlled to influence processing parameters such as the curing temperature for the flexible, compressed vaginal ring, as well as properties of the flexible, compressed vaginal ring itself, such as for example, flexibility and softness.

In some embodiments, a polymethacrylate suitable for use with the present invention has a $T_g$ of about 10° C. to about 50° C. In some embodiments, a polymethacrylate suitable for use with the present invention has a $T_g$ of about 10° C. to about 45° C. In some embodiments, a polymethacrylate suitable for use with the present invention has a $T_g$ of about 10° C. to about 40° C. In some embodiments, a polymethacrylate suitable for use with the present invention has a $T_g$ of about 10° C. to about 30° C. In some embodiments, a polymethacrylate suitable for use with the present invention has a $T_g$ of about 20° C. to about 40° C.

In some embodiments, the $T_g$ of a polymethacrylate, or a mixture thereof, can be used to determine the amount, by weight, of a plasticizer that should be added to the substantially homogeneous mixture of the present invention. For example, as the $T_g$ of a polymethacrylate for use with the present invention increases, the amount, by weight, of a plasticizer to be added to the mixture will increase, thereby maintaining a glass transition temperature of the homogeneous mixture within a desired range. In some embodiments, an amount of plasticizer is present in the substantially homogeneous mixture comprising a polymethacrylate and a plasticizer such that the mixture has a glass transition temperature not greater than about 80° C. In some embodiments, an amount of plasticizer is present in the substantially homogeneous mixture comprising a polymethacrylate and a plasticizer such that the mixture has a glass transition temperature not greater than about 60° C. In some embodiments, an amount of plasticizer is present in the substantially homogeneous mixture comprising a polymethacrylate and a plasticizer such that the mixture has a glass transition temperature not greater than about 40° C. In some embodiments, an amount of plasticizer is present in the substantially homogeneous mixture comprising a polymethacrylate and a plasticizer such that the mixture has a glass transition temperature not greater than about 37° C. (i.e., about "body temperature").

In some embodiments, the ratio of the polymethacrylate to the plasticizer is controlled on a weight basis. In some embodiments, the flexible, compressed intravaginal ring comprises a polymethacrylate and a plasticizer present in a ratio of about 1:1 to about 9:1, by weight. In some embodiments, the flexible, compressed intravaginal ring comprises a polymethacrylate and a plasticizer present in a ratio of about 2:1 to about 7:1 by weight. In some embodiments, the flexible, compressed intravaginal ring comprises a polymethacrylate and a plasticizer present in a ratio of about 3:1 to about 6:1 by weight. In some embodiments, the flexible, compressed intravaginal ring comprises a polymethacrylate and a plasticizer present in a ratio of about 3:1 to about 5:1 by weight. In some embodiments, the flexible, compressed intravaginal ring comprises a polymethacrylate and a plasticizer present in a ratio of about 4:1 by weight.

A "thickener" refers to a substance that can be added to a polymer or mixture to enhance one or more of its processing properties, such as, for example, viscosity. In some embodiments, thickeners suitable for use with the present invention are fibrous substances. In some embodiments, thickeners suitable for use with the present invention are substances capable of absorbing water. In some embodiments, thickeners suitable for use with the present invention are materials having a high surface area to volume ratio, or alternatively, a high free volume. For example, in some embodiments, a thickener suitable for use with the present invention can have a total surface area (i.e., a BET surface area) not less than about 100 m$^2$/g. In some embodiments, a thickener suitable for use with the present invention can have a total surface area not less than about 120 m$^2$/g, or alternatively, not less than about 150 m$^2$/g. In some embodiments, a thickener for use with the present invention can have a free volume of at least about 70%, or alternatively a free volume of at least about 80%. In some embodiments, a thickener can be a thixotropic agent (i.e., an agent that enhances stability upon standing), that can be useful for maintaining the homogeneity of a mixture from the time of mixing to compression. In some embodiments, a thickener can be used in conjunction with a plasticizer to modify the thermoelastic properties of the mixture and/or compressed ring. A thickener can also be useful for modifying the viscous properties of a mixture. For example, a binary mixture of a polymethacrylate and a plasticizer can be selected based on a desirable $T_g$ of the mixture, but the resulting mixture can have properties unsuitable for compressing, such as, for example, a low viscosity. Thus, in some embodiments, a thickener can enhance the viscous properties of a mixture, making it suitable for compression. Alternatively, a thickener can enhance one or more properties of the flexible, compressed ring composition. Thickeners suitable for use with the present invention include, but are not limited to, fumed silica (e.g., CAB-O-SIL®, Cabot Corp., Boston, Mass.; or AEROSIL®, Degussa AG, Frankfurt, Germany), colloidal silica, calcium silicate, gelatinized starch, microcrystalline cellulose, magnesium stearate, and combinations thereof.

In some embodiments, thickeners suitable for use with the present invention are traditionally used in compressed tablet compositions as glidants, which can reduce friction between compressed compositions and machine parts. Typically, glidants are present in a compressed tablet composition in a concentration of about 0.5% to about 2% by weight. However, in the present invention a thickener can be present at a concentration greater than 2% by weight. For example, in some embodiments, a thickener is present in the mixture at a concentration not less than about 2% by weight of the mixture. In some embodiments, a thickener is present in the mixture at a concentration of about 2% to about 20% by weight of the mixture. In some embodiments, a thickener is present in the mixture at a concentration of about 5% to about 20% by weight of the mixture, or alternatively, about 5% to about 15% by weight of the mixture, or alternatively, about 5% to about 10% by weight of the mixture, or alternatively, about 7.5% by weight of the mixture. Thus, in addition to decreasing friction between the mixture and machine parts during mixing and compression (i.e., acting as a glidant), thickeners can be used to control one or more thermoelastic or thermoviscous properties of the mixture and the resulting flexible, compressed ring composition. In some embodiments, thickeners make the mixture of the present invention particularly well-suited for compression at temperatures suitable for mass production, e.g., a compression temperature of about room temperature.

An "active agent" refers to a drug, protein, hormone, vitamin, nutritional supplement, or any other substance intended for use in the treatment, mitigation, cure or prevention of a disease or any other medical condition. In some embodiments, an active agent can be administered to a subject to treat a condition or a symptom thereof in a subject. For example, in some embodiments, the active agent is a component in a medicinal compound administered to treat one or more conditions, or the symptoms thereof, in a subject.

The flexible, compressed intravaginal ring of the present invention can be used to deliver multiple distinct types of active agents. Active agents for use with the present invention comprise active agents that have a localized effect, as well as systemically acting active agents that act at a point remote from the vaginal or urogenital tract. Active agents suitable for use with the present invention include, but are not limited to, a prostaglandin, a urinary incontinence agent, an analgesic, an anti-inflammatory agent, a hormonal agent, an anti-microbial, an anesthetic, an anti-osteoporosis agent, a peptide hormone, an enzyme, and combinations thereof. A hormonal agent can include, for example, an estrogen or progestin.

An "estrogen" refers to any of various natural or synthetic compounds that stimulate the development of female secondary sex characteristics and promote the growth and maintenance of the female reproductive system; or any other compound that mimics the physiological effect of natural estrogens. Estrogens suitable for use with the present invention also include compounds that can be converted to active estrogenic compounds in the uterine environment. For example, in some embodiments, a conjugated estrogen can be administered from a flexible, compressed intravaginal ring of the present invention. As used herein, the term "conjugated" refers to the sulfate ester, glucuronide ester, or mixed sulfate-glucuronide esters, of an estrogen. Estrogens suitable for use with the present invention also include pharmaceutically suitable salt forms of estrogens. In some embodiments, the salt can be a sodium, potassium, or 2-amino-2-(hydroxymethyl)-1,3-propanediol (Tris) salt. In some embodiments, an estrogen suitable for use with the present invention can be useful for Hormone Replacement Therapy (HRT) regimens. In some embodiments, an estrogen suitable for use with the present invention can be useful for the treatment of osteoporosis in a subject in need thereof.

A "progestin" refers to a progestogen, a progestational substance, or any pharmaceutically acceptable substance in the steroid art that generally possesses progestational activity including synthetic steroids that have progestational activity. Progestins suitable for use with the present invention can be of natural or synthetic origin. Progestins generally possess a cyclo-pentanophenanthrene nucleus. In some embodiments, progestins for use with the present invention can be useful for Hormone Replacement Therapy (HRT) regimens.

A "prostaglandin" is a biologically active compound derived from a polyunsaturated fatty acid having a length of twenty carbon atoms. Prostaglandins are classified based upon the specific structure of the pentane ring of the core prostaglandin chemical structure (e.g., prostaglandin A, prostaglandin B, prostaglandin D, prostaglandin E, prostaglandin F, and prostaglandin I). The distinct biological effects of the prostaglandin classes are due in part to the mediation of their activity by prostanoid receptors, which are expressed in a tissue-specific manner and specifically recognize the different classes of prostaglandins. In some embodiments of the present invention, the active agent is a substituted prostaglandin, a synthetic prostaglandin, or a prostaglandin analog. In some embodiments, the active agent is a prostaglandin, such as, for example, a prostaglandin of class A, E, or F, which has been shown to be useful in producing uterine contractions. In some embodiments, the active agent for use with the present invention comprises a mixture of the various prostaglandins, either alone or with added hormonal agents, oxytocin, polypeptides and the like.

A "urinary incontinence agent" is a compound that can be administered to treat urinary incontinence, stress incontinence, urge incontinence, overflow incontinence, mixed incontinence, reflex incontinence, decompensated bladder, detrusor instability, detrusor hyperreflexia, overactive bladder, continuous incontinence, dysfunctional urethra, urethral hypermobility, or the symptoms thereof. Symptoms associated with urinary incontinence include, but are not limited to, urinary tract infection, recurrent urinary tract infections, atrophic vaginitis, hematuria, gross pelvic prolapse, irritation during voiding, and combinations thereof.

An "analgesic" is a compound used to treat pain in a subject in need thereof. An analgesic administered using a flexible, compressed intravaginal ring of the present invention can be used to relieve local and/or systemic pain in a subject in need thereof.

An "anti-inflammatory agent" refers to a compound used to treat inflammation. Anti-inflammatory agents for use with the present invention include, but are not limited to, acetaminophen, aproxen, aspirin, diclofenac, etorolac, ibuprofen, indomethacin, ketoprofen, mefenamic acid, meloxicam, naproxyn, nimesulide, piroxicam, sulindac, and combinations thereof.

A "hormonal agent" refers to a compound having a cyclopentanophenanthrene nucleus structure, and which can affect metabolism and/or electrolyte excretion. Hormonal agents for use with the present invention include, but are not limited to, prednisolone, cortisone, cortisol, triamcinolone, and combinations thereof.

An "anti-microbial agent" refers to a compound possessing antibiotic, antifungal, antiprotozoal, and/or antiviral activity. Anti-microbial agents for use with the present invention include, but are not limited to, acyclovir, amantadine, amoxicillin, amphotericin B, ampicillin, atovaquone, azithromycin, cefazolin, cefepime, cefotaxime, cefotetan, cefpodoxime, ceftazidime, ceftizoxime, ceftriaxone, cefuroxime, cephalexin, chlorampehnicol, chlorotetracycline, clotrimazole, ciprofloxacin, clarithromycin, clindamycin, dapsone, dicloxacillin, doxycycline, erythromycin lactobionate, fluconazole, foscarnet, ganciclovir, gatifloxacin, imipenem, isoniazid, itraconazole, ketoconazole, metronidazole, nafcillin, nitrofurantoin, nystatin, oxytetracycline, penicillin, pentamidine, piperacillin, quinupristin-dalfopristin, rifampin, sulfonamide, tetracycline, ticarcillin/clavulanate, trimethoprim sulfamethoxazole, valacyclovir, vancomycin, and combinations thereof.

An "anesthetic" is a compound that blocks the passage of pain impulses in nerve pathways to the brain and induces a loss of sensation in one or more areas of the body without loss of vital functions. Anesthetics for use with the present invention include, but are not limited to, articaine, benoxinate, bupivacaine, dibucaine, lidocaine, mepivicaine, naepaine, piperocaine, procaine, prilocaine, tetracaine, and combinations thereof.

An "anti-osteoporosis agent" is a compound that can treat osteoporosis, or alternatively, promotes bone densification in a subject in need thereof. Anti-osteoporosis agents for use with the present invention include, but are not limited to, calcitonin, raloxifene, teriparatide, and combinations thereof.

A "peptide hormone" is a compound having a peptide or polypeptide sequence, and which exhibits endocrine functionality.

An "enzyme" is a compound with a polypeptide structure that functions as a biological catalyst.

In some embodiments, the flexible, compressed intravaginal ring further comprises an excipient. As used herein, an "excipient" refers to a substance that is used in the formulation of pharmaceutical compositions, and, by itself, generally has little or no therapeutic value. One of skill in the art will recognize that a wide variety of pharmaceutically acceptable excipients can be used with the present invention including those listed in the *Handbook of Pharmaceutical Excipients*, Pharmaceutical Press 4th Ed. (2003) and *Remington: The Science and Practice of Pharmacy*, Lippincott Williams & Wilkins, 21st Ed. (2005), which are incorporated herein by reference in their entirety. As used herein, the term "pharmaceutically acceptable" refers to those compounds, materials, and/or compositions which are, within the scope of sound medical judgment, suitable for contact with the tissues of human beings and animals without excessive toxicity, irritation, allergic response, or other possible complications commensurate with a reasonable benefit/risk ratio. In particular, excipients for use with the present invention include, but are not limited to, a diluent, a binder, a lubricant, an antioxidant, and combinations thereof.

A "diluent" refers to an inert substance that can be added to the substantially homogeneous mixture prior to compressing to increase its bulk and make the mixture more suitable for compressing into a flexible, compressed intravaginal ring. Diluents for use with the present invention include any inert substance suitable for compressing with a polymethacrylate polymer or mixtures thereof. Diluents suitable for use with the present invention include, but are not limited to, calcium phosphate dibasic, calcium phosphate tribasic, calcium carbonate, calcium sulfate, microcrystalline cellulose, powdered cellulose, kaolin, and combinations thereof.

A "binder" refers to an agent that can improve the cohesive qualities of a mixture such as, for example, during compression. Binders suitable for use in the present invention include, but are not limited to, polyethylene glycol, polyvinylpyrrolidone (e.g., povidone), and combinations thereof.

A "lubricant" refers to an agent that can prevent adhesion of a mixture to surfaces such as, for example, mixing equipment and dies and punches. A lubricant can also reduce interparticle friction within a powdered mixture, as well as ease the removal (i.e., ejection) of a flexible, compressed mixture from a die cavity following compression. Lubricants suitable for use in the present invention include, but are not limited to, magnesium stearate, calcium stearate, zinc stearate, stearic acid, leucine, glyceryl behenate, sodium lauryl sulfate, sodium stearyl fumarate, and combinations thereof.

An "antioxidant" refers to an agent that can prevent the oxidation of an active agent, a polymer, or other ingredients present in an intravaginal ring or mixture of the present invention. Antioxidants suitable for use in the present invention include, but are not limited to, adipic acid, alpha lipoic acid, ascorbyl palmitate, biotin, boron, butylated hydroxytoluene (e.g., 2,6-di-tert-butyl-para-cresol), butylated hydroxyanisole (e.g., tert-butyl-4-hydroxyanisole), carotenoids, calcium citrate, sodium metabisulfate, tocopherols, and combinations thereof.

Figure 1B:
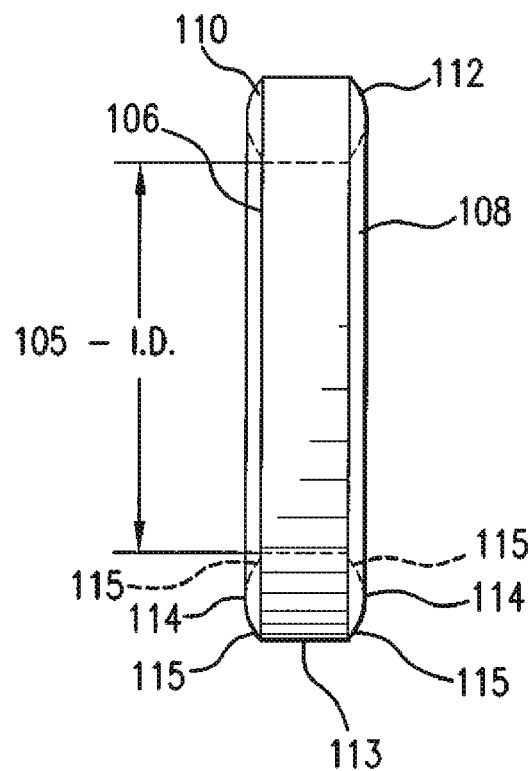

A flexible, compressed intravaginal ring 100 of the present invention is shown in FIG. 1A and FIG. 1B. The flexible, compressed intravaginal ring 100 is shaped like a ring and has an inner opening 102. The intravaginal ring 100 has an outer diameter (O.D.) 104 and an inner diameter (I.D.) 105. In some embodiments, the outer diameter 104 can be about 2.1 inches and the inner diameter 105 can be about 1.45 inches. However, the intravaginal ring 100 can vary in size, having an outer diameter 104 of about 0.75 inches to about 2.5 inches, and having an inner diameter 105 of about 0.5 inches to about 2.25 inches.

As shown in FIG. 1B the intravaginal ring 100 has a top surface 106, a bottom surface 108, and an outer surface 113. In some embodiments, the top and bottom surfaces 106 and 108, respectively, have chamfered edges 110 and 112, respectively, and a cup 114 having lands 115 on either side of the cup 114. The radius of curvature for the cup can be about 0.0213 inches and the cup depth can be about 0.06 inches. The length of the lands can be about 0.015 inches. However, the top and bottom surfaces 106 and 108, respectively, can be rounded, flat, elliptical, or any other desired shape that would be apparent to one of ordinary skill in the art.

Methods of Production

The present invention is also directed to a process for preparing a flexible, compressed intravaginal ring, the process comprising:

mixing a polymethacrylate having a glass transition temperature, a plasticizer, a thickener, and an active agent at a temperature above the glass transition temperature of the polymethacrylate to form a substantially homogeneous mixture; and compressing the substantially homogeneous mixture at a temperature below the glass transition temperature of the mixture to fox in a flexible, compressed intravaginal ring.

The present invention is also directed to a product prepared by the process of the present invention.

The substantially homogeneous mixtures for use with the present invention can be prepared using a wide variety of methods for mixing the ingredients, including any method recognized by artisans skilled in the methods of mixing ingredients, that results in a substantially homogeneous mixture suitable for compressing. Such methods include, but are not limited to, the following:

Dry powder blending: dry ingredients, except for the lubricant, if one is present, are combined and mixed using a suitable low shear diffusion-type mixer, or other mixing device, for a period of time sufficient to result in a substantially homogeneous dry mixture. In some embodiments, a lubricant is added after an initial period of mixing, which can be followed by remixing, at least until a second substantially homogeneous dry mixture is formed, which can be compressed to form a flexible, compressed intravaginal ring of the present invention using, for example, a compression press.

Alternatively, the dry ingredients, except for the lubricant, are combined sequentially and mixed for a sufficient period of time after each ingredient is sequentially added to the mixture, to achieve a substantially homogeneous mixing of the ingredients. Sequential mixing of the ingredients can be followed by compressing the substantially homogeneous mixture to form flexible, compressed intravaginal rings using, for example, a CARVER® Laboratory Press (Fred S. Carver, Inc., New York, N.Y.). In some embodiments, sequential mixing comprises geometric dilution.

In some embodiments, the process of mixing the ingredients to form a substantially homogeneous mixture comprises an intermediate number of steps to the mixing methods of dry powder blending and geometric dilution. For example, in some embodiments, the active agent is combined and mixed with one dry ingredient, except for a lubricant, for a period of time sufficient to form a substantially homogeneous mixture of the active agent and a first ingredient. In some embodiments, this is followed by a sequential or one-time addition of some, or all, of the remaining ingredients. Thus, the active agent is pre-mixed with one other inactive ingredient prior to addition of the remaining ingredients. The substantially homogeneous mixture comprising all of the ingredients is then compressed into solid intravaginal rings using, for example, a compression press.

Wet granulation: an active agent, a bulking agent, and other ingredients are dissolved or suspended in a liquid medium, and mixed using a high shear mixing apparatus until a substantially homogeneous paste is formed. The substantially homogeneous paste can then be dried, ground, and sized to form a substantially homogeneous dry granulation or powder, which can then be compressed to form flexible, compressed intravaginal rings of the present invention using methods and equipment known to those skilled in the art of dry powder compression.

In some embodiments, an active agent and a plasticizer are mixed for a period of time suitable to form a first substantially homogeneous mixture. In some embodiments, the first substantially homogeneous mixture comprises dissolving an active agent in a plasticizer. A thickener can then be added as mixing continues. After the total amount of thickener is added to the mixture, the contents are then mixed for a period of time sufficient to produce a second substantially homogeneous mixture. A polymethacrylate can then added to the second mixture, followed by mixing for a time sufficient to produce a third substantially homogeneous mixture. A lubricant, such as magnesium stearate, can then be added, followed by mixing for a time sufficient to form a final substantially homogeneous mixture. The final substantially homogeneous mixture can be then compressed to form a flexible, compressed intravaginal ring of the present invention.

In some embodiments, the mixing of the mixture is performed at a temperature above the glass transition temperature of the polymethacrylate. Not being bound by any particular theory, controlling the temperature during mixing in this manner permits the components of the mixture in addition to the polymethacrylate (i.e., the plasticizer and thickener) to become intimately mixed with the polymethacrylate on a molecular level, and permitting a highly homogeneous mixture to be rapidly formed.

In some embodiments, the process of the present invention further comprises cooling the substantially homogeneous mixture to a temperature below the glass transition temperature of the mixture. In some embodiments, the process of the present invention further comprises cooling the substantially homogeneous mixture to about 25° C. In some embodiments, the process of the present invention comprises cooling the substantially homogeneous mixture to about 20° C., or alternatively, cooling the substantially homogeneous mixture to about 15° C., or to about 10° C., or to about 5° C., or to about 0° C., or to about –5° C., or to about –10° C., or to about –15° C., or to about –20° C.

Cooling can be achieved using any variety of means suitable for use in a manufacturing environment, for example, flash cooling, refrigerating, convection cooling, immersion cooling, and combinations thereof. In some embodiments, cooling is performed in a "batch" mode (i.e., multiple units are cooled simultaneously).

Figure 7:
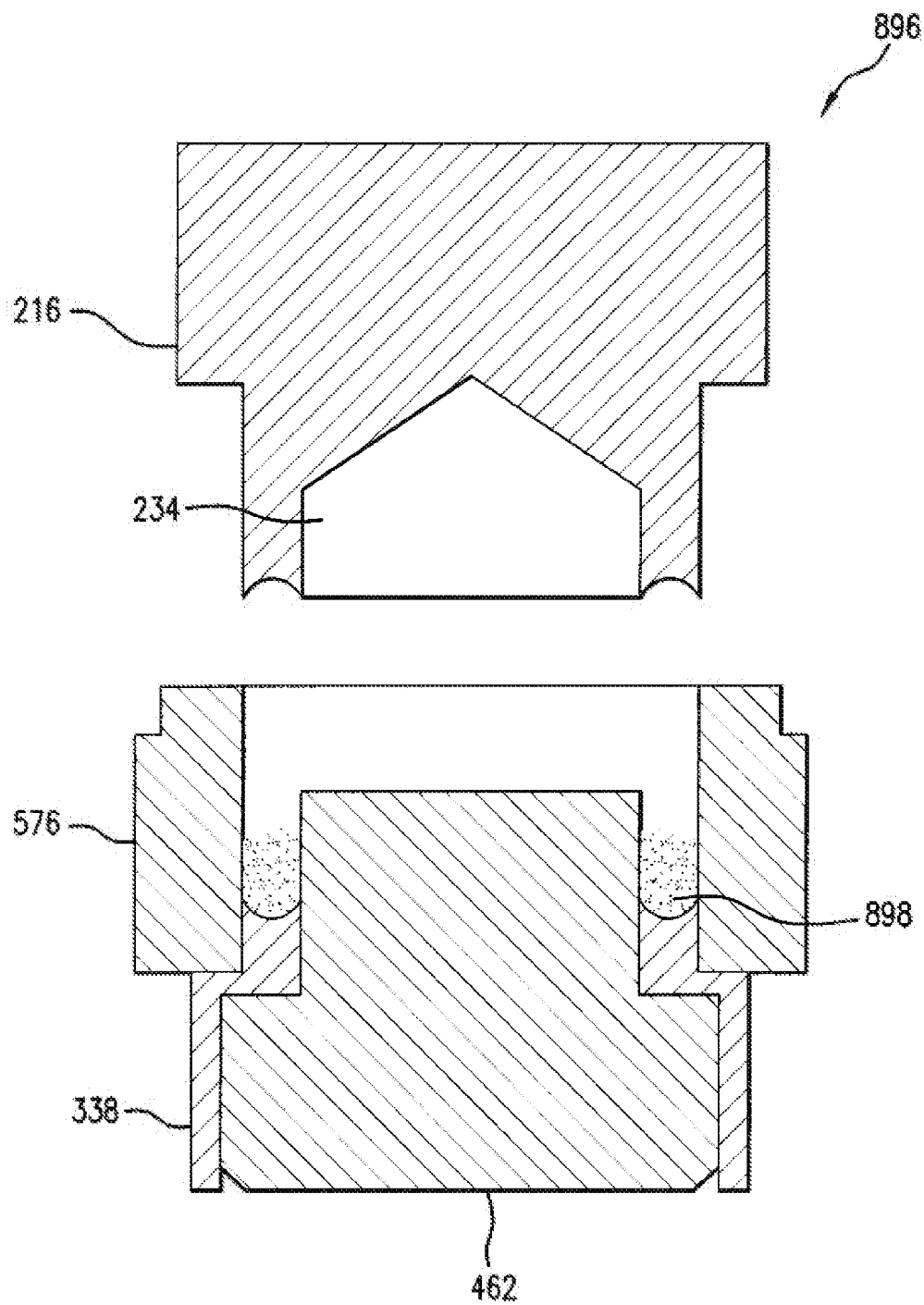
FIG. 7 is a cross-sectional view of the compression tooling apparatus before compression.
Figure 8:
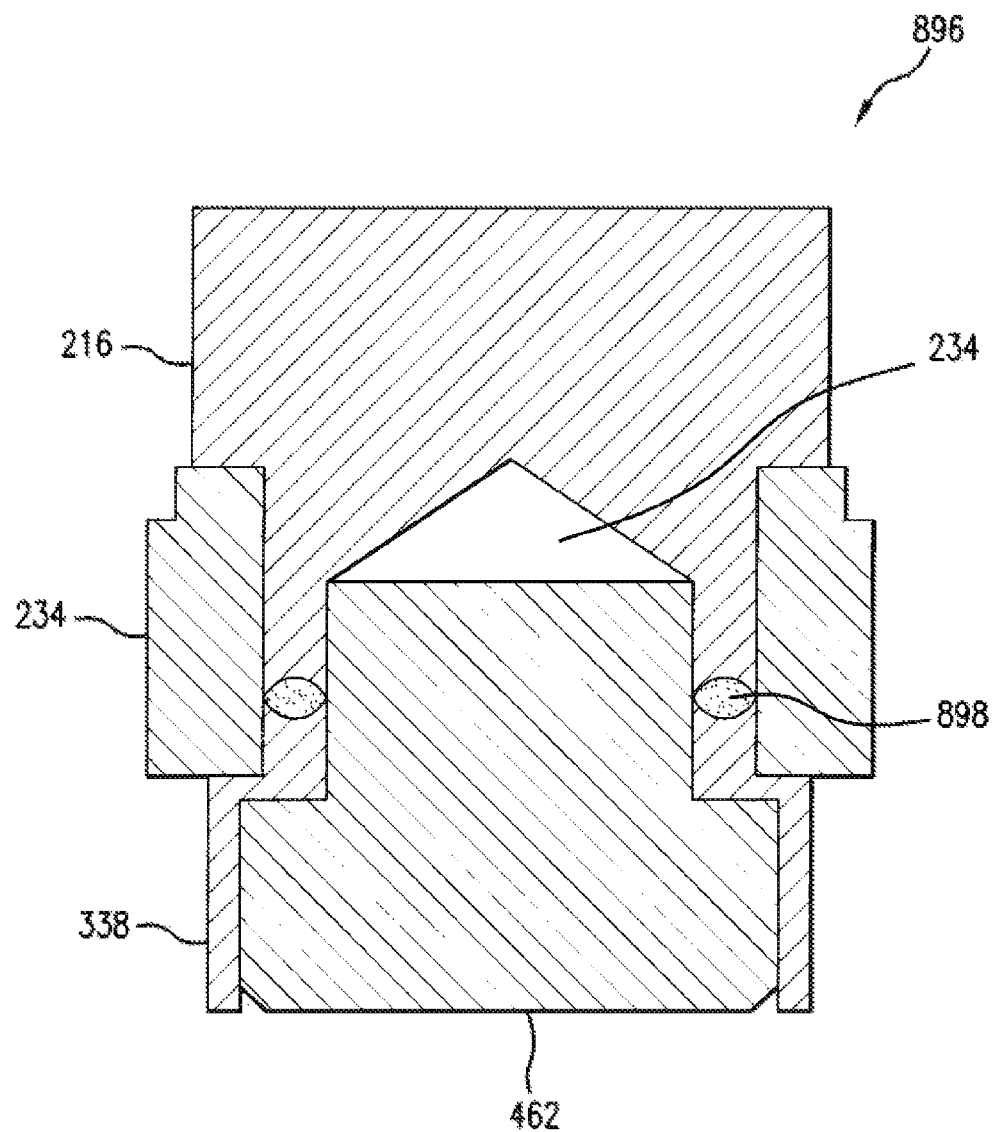
FIG. 8 is a cross-sectional view of the compression tooling apparatus during compression.

The process of compressing is achieved utilizing a compression tooling apparatus comprising an upper punch, a lower punch, a core rod, and a die, as shown in FIGS. 2-5, respectively. FIG. 7 and FIG. 8 show all the parts of the compression tooling apparatus assembled together for compressing a substantially homogeneous mixture into a flexible, compressed intravaginal ring. Below is a description of the various components. All dimensions for the various parts of the compression tooling given below are for utilization in a CARVER® Laboratory Press. However, the compression tooling apparatus is not limited to use with a CARVER® Laboratory Press and the present invention is also particularly well-suited for use with a batch compression apparatus, such as a STOKES® Single Station Press (Stokes-Merrill, Inc., Corporation, Bristol, Pa.). One or more of the dimensions can change as a function of the production tooling utilized.

Figure 2:
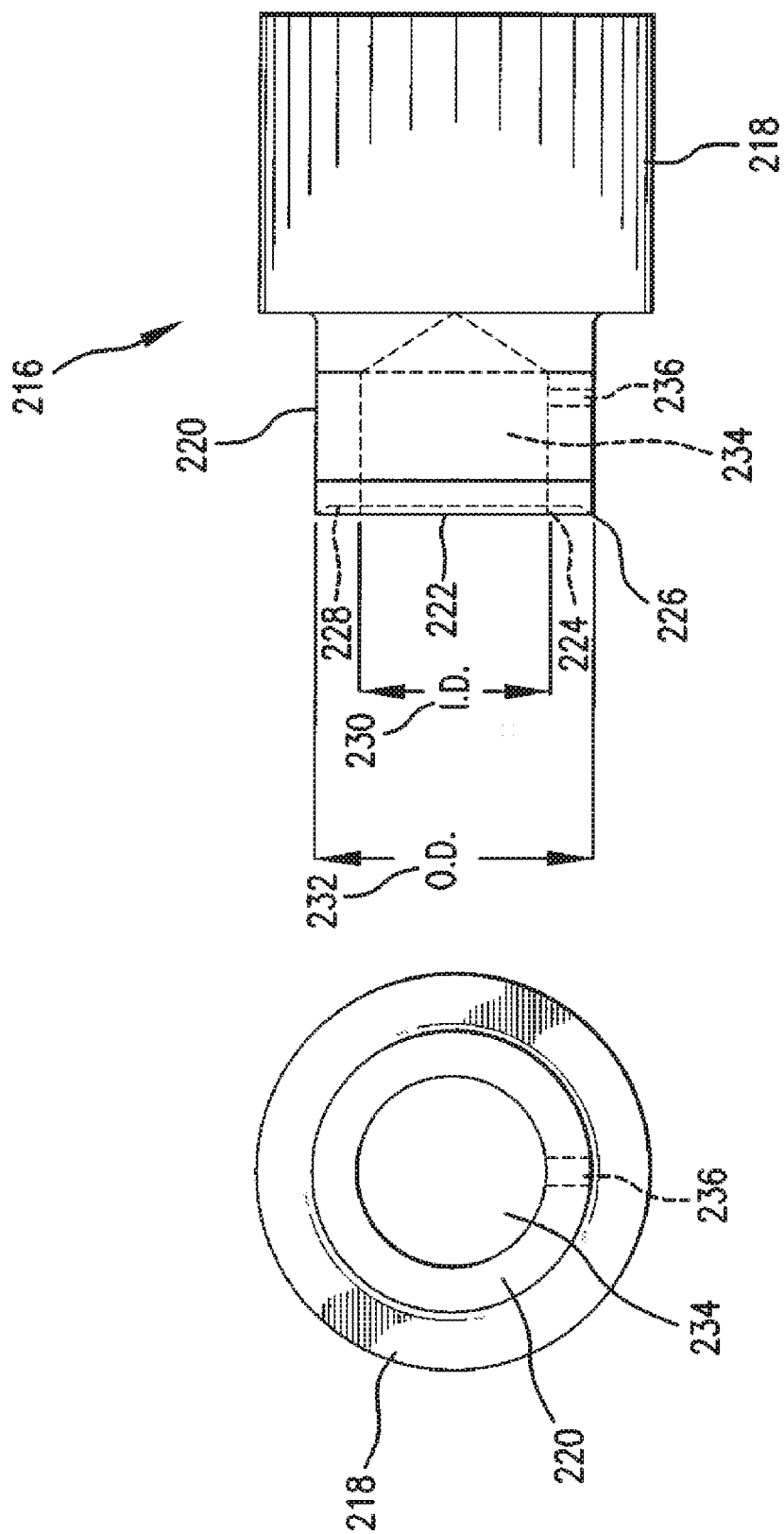
FIG. 2-FIG. 6 are views of the compression tooling apparatus used to make a flexible, compressed intravaginal ring of the present invention.

The upper punch 216, as shown in FIG. 2, comprises a punch base 218, and a punch extension 220 that has a punch face 222. The punch face 222 has an inner edge 224 and a sharp outer edge 226 with a cup 228 located in between. The cup 228 has a mirror finish and is shaped according to the desired shape of the flexible, compressed intravaginal ring. For example, in some embodiments, the cup 228 can be concave with a cup depth of about 0.06 inches and has lands on either side that can be about 0.015 inches. The inner diameter (I.D.) 230 of the punch face 222 can be about 2.098 inches and the outer diameter (O.D.) 232 of the punch face 222 can be about 1.456 inches. The punch extension 220 has a cavity 234 for housing a core rod 462 (see FIG. 4) during compression and an air hole 236 that extends into the cavity 234, and which allows air to escape the cavity 234 during compression.

The following dimensions of the upper punch 216 are for one exemplary embodiment and are not meant to be limiting. The upper punch 216 can have an overall length of about 4.0 inches. The punch base 218 can have a diameter of about 3.0 inches. The punch extension 220 can have a length of about 1.625 inches and where it meets the punch base 218, a diameter of about 2.05 inches. In some embodiments, the junction of the punch extension 220 and the punch base 218 has a maximum radius of curvature of 0.063 inches. The corners of the punch base 218 can have a 0.015 inch×45° chamfer. The punch face 222 can have a length of about 0.25 inches. The cavity 234 can extend into the punch extension 220 for about 1.125 inches until it tapers off. The diameter of cavity 234 can also expand from about 1.456 inches at the punch face 222 to about 1.50 inches at the point where the cavity 234 tapers off. A center of air hole 236 can be located about 1 inch from the punch face and can have a diameter of about 0.25 inches.

Figure 3:
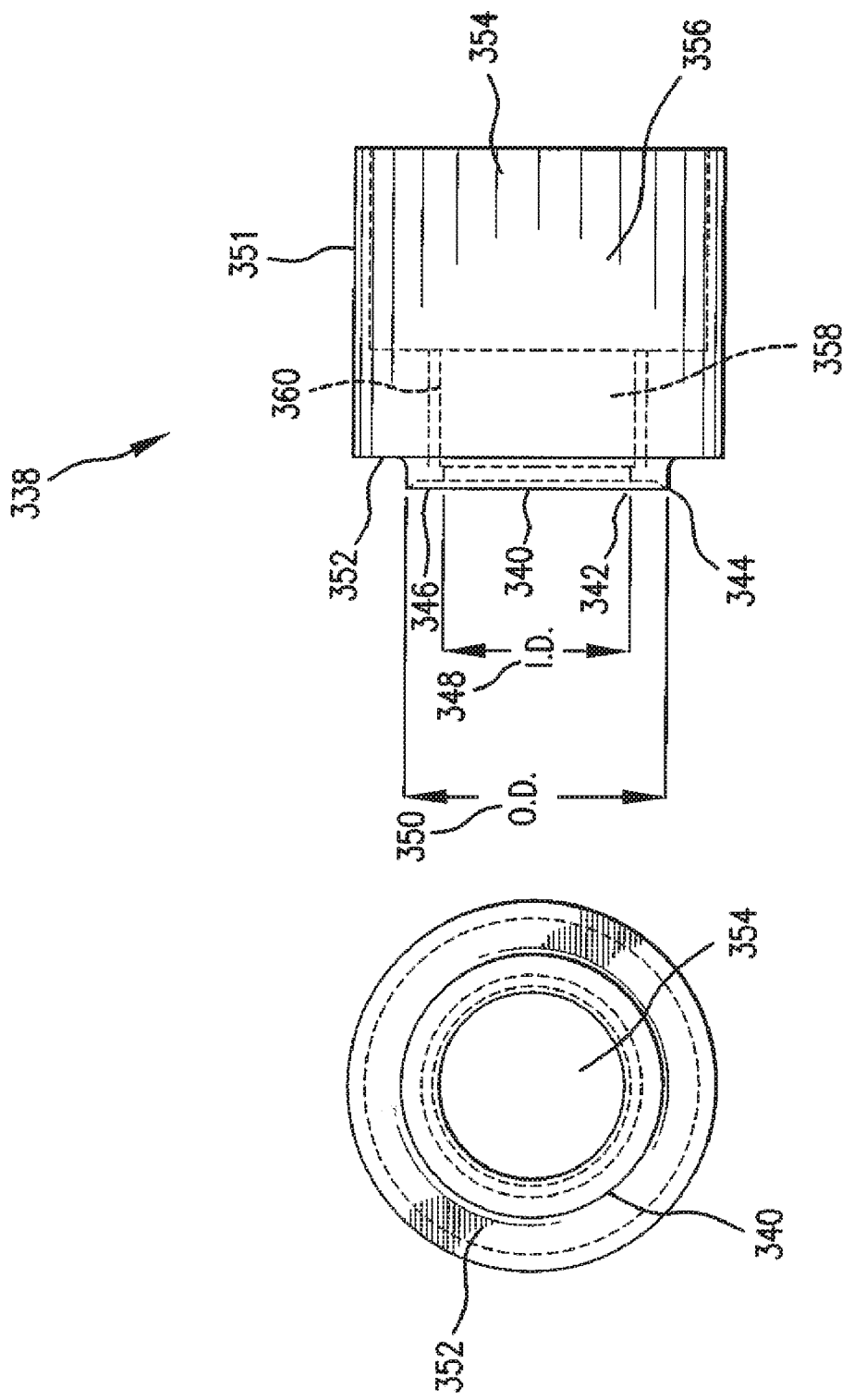

The lower punch 338, as shown in FIG. 3, comprises a punch face 340 and a punch base 351. The punch face 340 has an inner edge 342 and a sharp outer edge 344 with a cup 346 located in between. The cup 346 has a mirror finish and is shaped according to the desired shape of the flexible, compressed intravaginal ring. For example, in some embodiments, the cup 346 can be concave with a cup depth of about 0.06 inches and have lands on either side that can be about 0.015 inches. The inner diameter (I.D.) 348 of the punch face 340 can be about 2.098 inches and the outer diameter (O.D.) 350 of the punch face 340 can be about 1.456 inches.

The punch base 351 has a shoulder 352 on which a die 576 (see FIG. 5) sits during compression and a cylindrical bore 354. The cylindrical bore 354 comprises a base housing 356, a rod housing 358 and threads 360. The cylindrical bore 354 is designed to allow insertion of a core rod 462 (see FIG. 4), which can be adjusted to a desired height by rotating the core rod 462 in the cylindrical bore 354.

The following dimensions of the lower punch 338 are for one exemplary embodiment and are not meant to be limiting. The lower punch 338 can have an overall length of about 2.937 inches. The junction of the punch face 340 and the punch base 351 can have a maximum radius of curvature of 0.031 inches. The corners of the punch base 351 can have a 0.015 inch×45° chamfer. The diameter of the punch base 351 can be about 3.0 inches. The diameter of the base housing 356 can be about 2.75 inches. The rod housing 358 can have a length of about 1.0 inches and have a drill and tap for 1.75 to 5.0 threads/inch UNC (Uniform Coarse) threads. The punch face 340 can have a length of about 0.25 inches.

Figure 4:
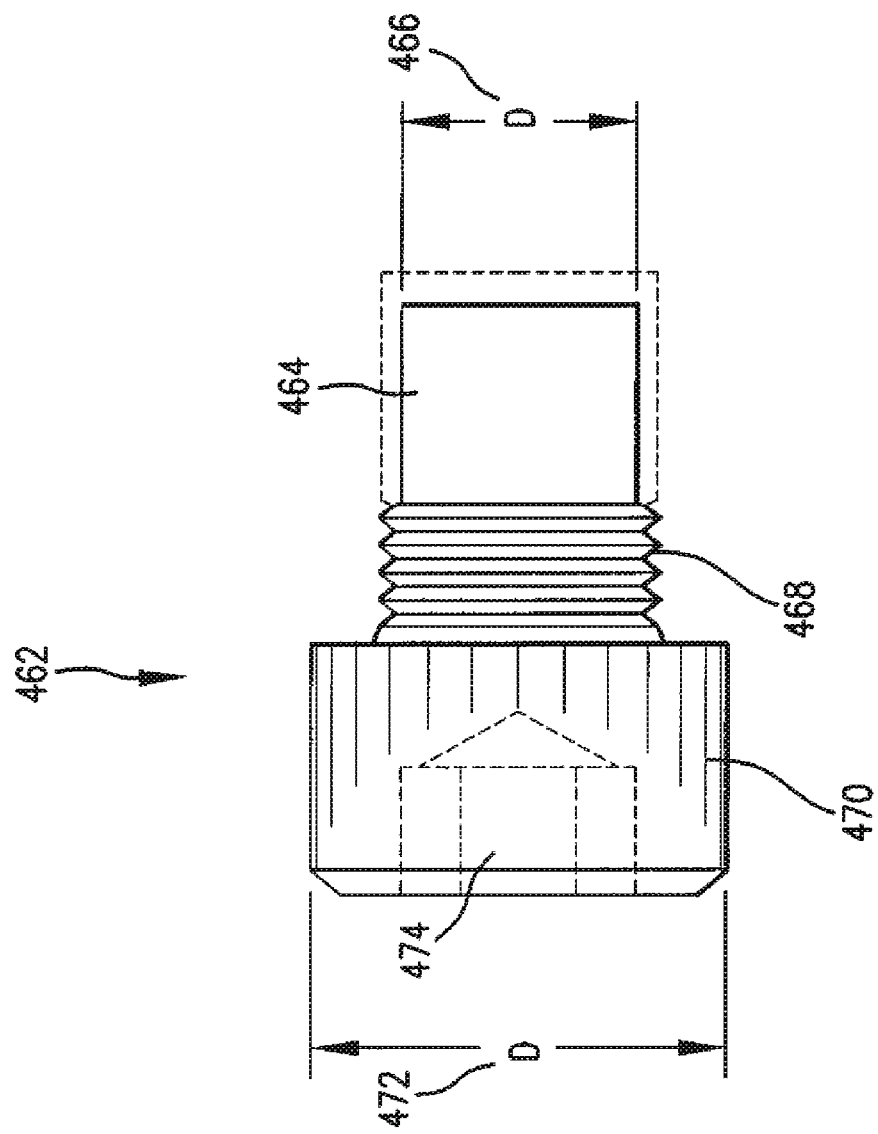
Figure 4:
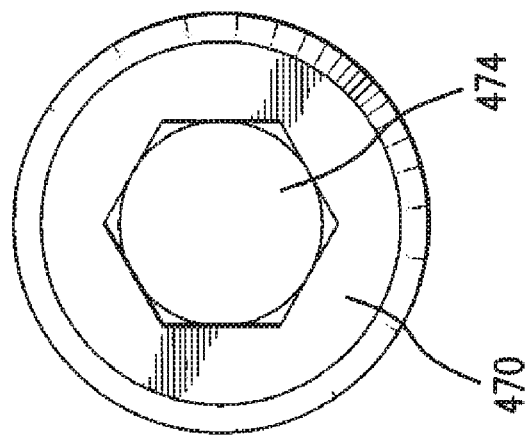

The core rod 462, as shown in FIG. 4, comprises a rod 464, threads 468 and a base 470. The core rod 462 is screwed into the cylindrical bore 354 of the lower punch 338 such that the rod 464 will go into the cavity 234 of the upper punch 216 during operation of the compression tooling apparatus. The base 470 has a hexagonal socket 474 for rotating and adjusting the core rod 462 to the desired location.

The diameter of the rod 464 is sized to control the inner diameter 105 of the flexible, compressed intravaginal ring 100. In some embodiments, the rod 464 has a diameter 466 of about 1.454 inches adjacent the threads 468 and tapers down to about 1.450 inches. The length of the rod 464 and threads 468 can be about 2.3 inches with a purchased length of about 2.5 inches. The corners of the rod 464 can have a 0.031 inch×45° chamfer. The threads can have a length of 0.95 inches and can be 1.75 to 5.0 threads/inch UNC (Uniform Coarse) threads. The base 470 can have a length of about 1.75 inches and a diameter 472 of about 2.625 inches.

Figure 5:
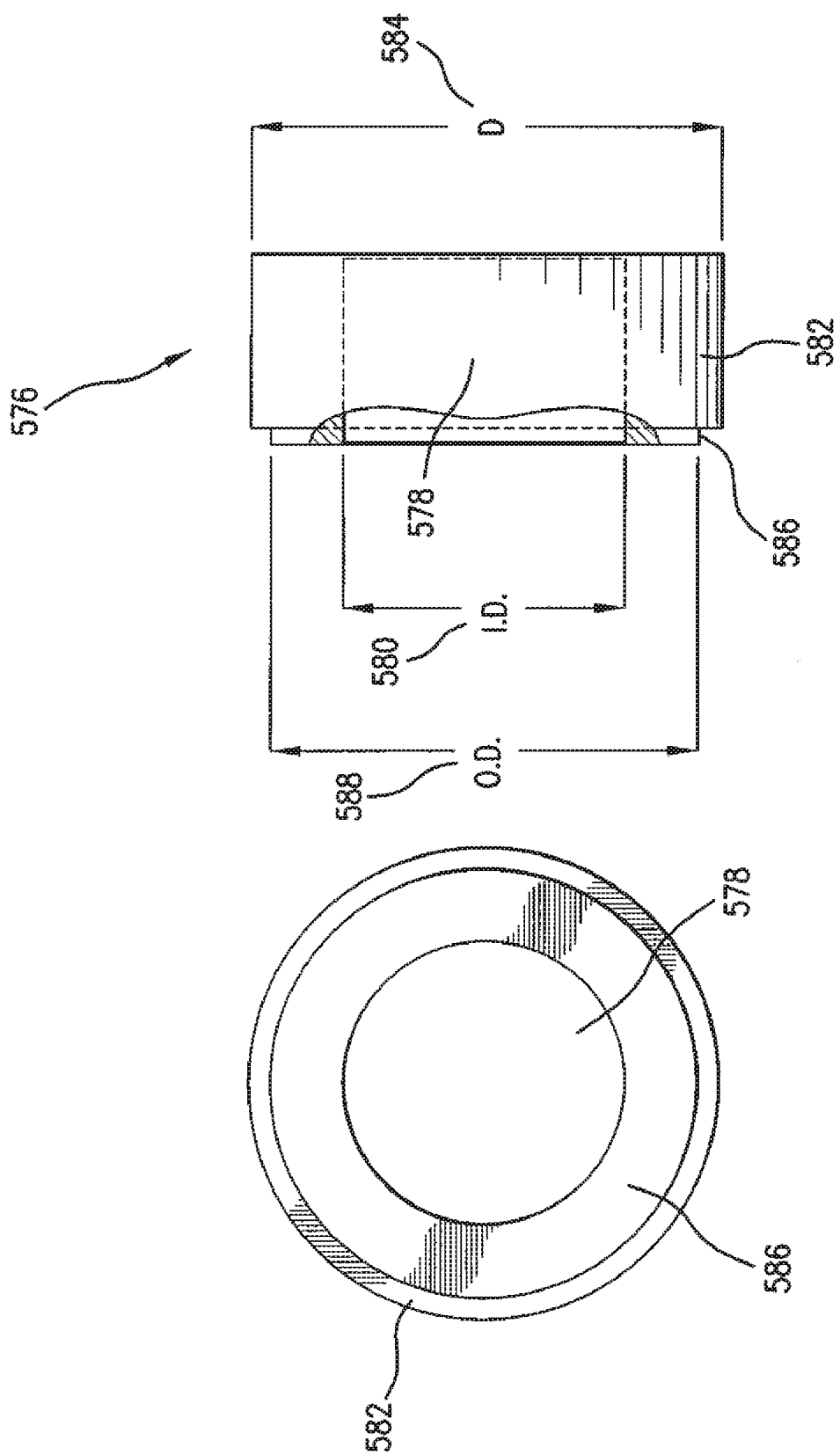

The die 576, as shown in FIG. 5, comprises a cavity 578, a base 582, and a raised extension 586. The cavity 578 of the die 576 is sized so the punch face 340 of the lower punch 338 and the punch face 222 of the upper punch 216 fit within the cavity 578. The cavity has an inner diameter (I.D.) 580, which is sized to control the outer diameter 104 of the flexible, compressed intravaginal ring 100. In one exemplary embodiment, the overall diameter (D) 584 of the die 576 can be about 3.5 inches, the inner diameter (I.D.) 580 of the raised extension 586 (diameter of the cavity 578) can be about 2.1 inches and the outer diameter (O.D.) 588 of the raised extension 586 can be about 3.24 inches. The die 576 can have an overall length of about 1.5 inches and the length of the raised extension 586 can be about 0.125 inches.

Figure 6:
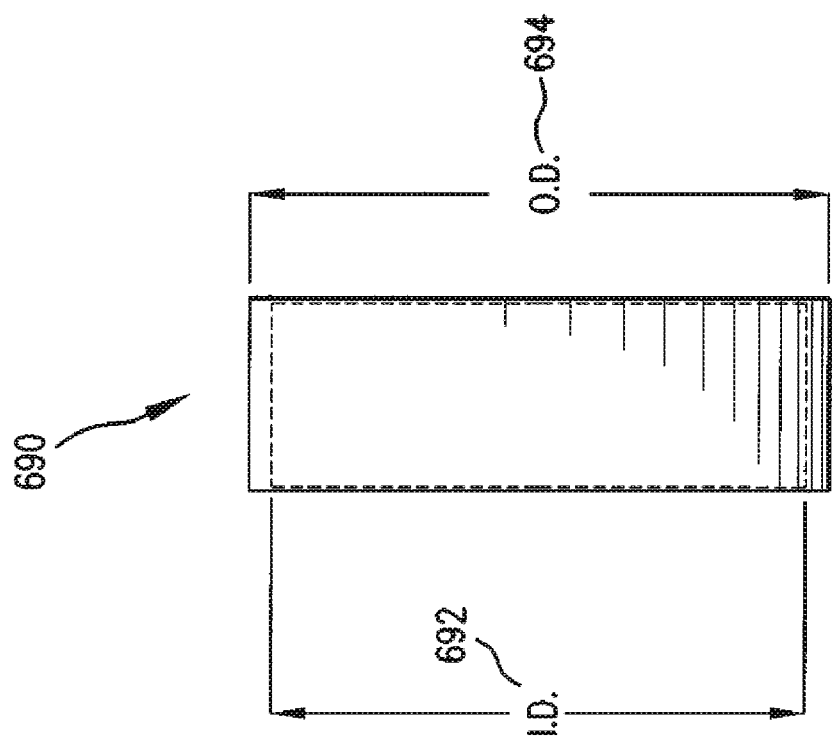
Figure 6:
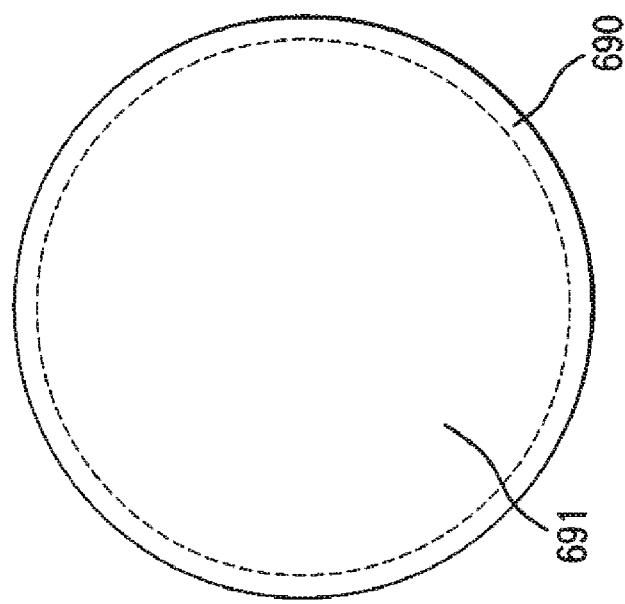

The process for compressing the intravaginal ring is generally outlined in FIGS. 6, 7 and 8. The core rod 462 is inserted in the cylindrical bore 354 of the lower punch 338 and adjusted to the desired position. The rod 464 extends beyond the punch face 340 of the lower punch 338. The lower punch 338 is positioned within the die 576 such that the base 582 of the die 576 sits flat on the shoulder 352 of the lower punch 338 and the punch face 340 of the lower punch 338 is within the cavity 578 of the die 576.

FIG. 7 shows the compression tooling apparatus 896 assembled together prior to compression. The compression tooling apparatus 896 can be used, for example, with a CARVER® Laboratory Press or any commercial semi-automatic press known to one of ordinary skill in the art. The various components of the compression tooling apparatus 896 are made of steel, for example, S7 steel, 308 steel, or 440 steel.

Once the core rod 462 and the lower punch 338 are positioned, the substantially homogenous mixture 898 is discharged into the die 576 onto the punch face 340 of the lower punch 340. The discharge can be accomplished using any conventional method known in the art, such as manually or utilizing a feeding chute.

Next the mixture 898 is compressed between the punch faces 222 and 340 of the upper and lower punches 216 and 338, respectively, as shown in FIG. 8. During compression, the core rod 462 enters into the cavity 234 of the upper punch 216. The size and shape of the flexible, compressed intravaginal ring is determined by the inner diameter 580 of the cavity 578 of the die 576, the diameter 466 of the rod 464, and the contours of the upper and lower punch faces 222 and 340, respectively. Once the compression is complete the upper and lower punches 216 and 338, respectively, are separated. Then the flexible, compressed intravaginal ring is ejected from the lower punch 338.

In one embodiment, ejection of the ring 100 is accomplished with the use of an ejector die 690, as shown in FIG. 6. The ejector die 690 has a cavity 691. The ejector die 690 can have a length of about 1.25 inches, an inner diameter (I.D.) 692 of about 3.25 inches, and an outer diameter (O.D.) 694 of about 3.5 inches. The ejector die 690 is positioned on top of the die 576. The lower punch 338 pushes the flexible, compressed intravaginal ring 100 out of the die 576 and into the cavity 691 of the ejector die 690. The ejector die 690 holds the flexible, compressed intravaginal ring 100 by friction until it is removed by any conventional means.

Alternatively, the ejection of the ring can be accomplished by moving the lower punch relative to the die and core rod such that the punch face of the lower punch is brought even with an upper surface of the die, thereby pushing the ring out of the die. The flexible, compressed intravaginal ring can then be swept off the die, for example with the feeding chute.

In some embodiments of the process of the present invention, the compressing is performed at a temperature below the glass transition temperature of the substantially homogeneous mixture. In some embodiments, the compressing is performed at a temperature of about 5° C. to about 40° C. In some embodiments, the compressing is performed at a temperature of about 5° C. to about 30° C. In some embodiments, the compressing is performed at a temperature of about 5° C. to about 25° C., or alternatively, at a temperature of about 5° C. to about 15° C. This can make the process of the present invention particularly well-suited for use in a batch manufacturing environment.

Not being bound by any particular theory, the process of the present invention can be optimized based on the plastic and elastic properties of the mixture. The plastic and elastic properties of the mixture are substantially inversely related to one another. Thus, as the plasticity of a mixture increases, its elasticity decreases. During compression, the plasticity of the substantially homogeneous mixture permits the mixture to retain the shape that is formed by compressing the mixture. Generally, the plasticity of a mixture increases as the temperature of the mixture is increased, and in particular, the plasticity can increase rapidly above the $T_g$ of a mixture. Thus, one of ordinary skill in the art of compression would expect that a more efficient compression process would occur at a temperature above the $T_g$ of a plastic mixture. However, the process of the present invention compresses a mixture at a temperature below the $T_g$ of the mixture. While controlling the temperature in this manner can make compressing more difficult (i.e., can require greater pressure for compression), the present invention has found that the overall process becomes more efficient. This increase in efficiency results largely from the ease with which the mixture can be flowed into the punch and die, and the flexible, compressed intravaginal ring can be removed from the punch and die. For example, the time required for flowing the mixture into the punch and die prior to compressing can be greatly reduced by maintaining the mixture at a temperature below its glass transition temperature. Moreover, compressing at a temperature below the $T_g$ of the mixture permits the resulting flexible, compressed ring to be easily ejected from the punch and die after compressing. Moreover, maintaining a temperature below the $T_g$ of the mixture avoids problems such as plastic deformation of the ring during its removal from the punch and die. Thus, the process of the present invention balances the plastic properties of the mixture that result in excellent compaction during compression, and the elastic properties of the ring that allow it to be easily removed from the punch and die after compression. Furthermore, the elastic properties of the flexible, compressed ring allow it to be flexed without losing its shape, and the flexible, compressed intravaginal rings of the present invention are pliable (i.e., flexible) at room temperature (e.g., about 23° C.) and at body temperature (e.g., about 37° C.).

The components of the flexible, compressed intravaginal ring are also selected to allow the ring to be fabricated using a rapid, cost-efficient compression process. For example, in some embodiments, the polymethacrylate for use with the present invention can be semi-viscous at room temperature, and compressing a mixture containing the polymethacrylate at a temperature below the $T_g$ of the mixture could require elaborate measures such as enclosing the compression tool in a refrigerated room or box, jacketing the compression apparatus with coolant lines, or other costly measures undesirable for use in a manufacturing environment. In these cases a suitable amount of a thickener can be added to the mixture to modify its thermo-elastic properties, or the mixture can be cooled to below its $T_g$ prior to compression, so that the mixture can be compressed at about room temperature. Thus, the mixture and process of the present invention are particularly well-suited for low cost manufacturing of flexible, compressed rings under mild conditions.

While there can be other advantages to compressing at a temperature above the $T_g$ of the mixture, such as, for example, simultaneously compressing and curing, such processes above the $T_g$ of the mixture typically require several minutes up to an hour to give a reproducible shape, and can make ejection of the ring difficult. Thus, compared to previous compression processes, the process of the present invention provides a method for forming a flexible, compressed ring in an efficient, reproducible manner that is highly efficacious for manufacturing. Advantages in processing time that could be had by simultaneously compressing and curing can also be compensated for by performing curing in a "batch" mode. Thus, the process of the present invention represents an improvement over other manufacturing processes for preparing intravaginal rings, which can manufacture the rings at a rate of about 10 to about 60 per hour. For example, in the process of the present invention the time of compression can be about 0.5 seconds to about 10 seconds, or alternatively, about 1 to about 5 seconds. In some embodiments, the flexible, compressed intravaginal rings of the present invention can be produced at a rate of at least about 600 per hour. In some embodiments, the flexible, compressed intravaginal rings of the present invention can be produced at a rate of at least about 800 per hour. In some embodiments, the flexible, compressed intravaginal rings of the present invention can be produced at a rate of at least about 1000 per hour.

In some embodiments, the process of the present invention further comprises directly following the compressing, curing the flexible, compressed intravaginal ring. As used herein, "curing" refers to a process useful to solidify, harden, or cross-link a substantially homogeneous flexible, compressed composition of the present invention. Curing can comprise heating, drying, crystallizing, cross-linking, photo-curing (e.g., exposing to monochromatic or broad-band ultraviolet, visible, or infrared light,) or combinations thereof. In some embodiments, curing comprises heating the flexible, compressed intravaginal ring to a temperature above the $T_g$ of the mixture. In some embodiments, curing comprises heating at a temperature above the $T_g$ of the flexible, compressed intravaginal ring (i.e., the compressed mixture comprising a poly (methacrylate), a plasticizer, a thickener, and an active agent). In some embodiments, curing comprises heating at a temperature of about 20° C. to about 110° C. In some embodiments, curing comprises heating at a temperature of about 20° C. to about 100° C., about 20° C. to about 90° C., about 25° C. to about 100° C., about 25° C. to about 90° C., about 25° C. to about 80° C., or about 30° C. to about 80° C.

The duration of curing can vary. In some embodiments, curing is for about 15 minutes to about 48 hours. In some embodiments, curing is for about 30 minutes to about 36 hours, or alternatively about 1 hour to about 24 hours. In some embodiments, curing is for about 2 hours to about 12 hours.

The conditions used for curing can be controlled and varied. In some embodiments, curing is conducted at ambient pressure, under an atmosphere of air. In some embodiments, curing is conducted under a controlled atmosphere (e.g., under an atmosphere comprising less than about 20%, by volume, of oxygen or another oxidant). In some embodiments, curing is conducted under an inert atmosphere (e.g., under an atmosphere comprising one or more non-reactive gases, such as for example, nitrogen, argon, neon, krypton, xenon, and mixtures thereof.) In some embodiments, curing is conducted at a reduced pressure (e.g., under vacuum). In some embodiments, curing is conducted under reducing conditions (e.g., under an atmosphere comprising a reducing gas, such as for example, carbon monoxide, hydrogen, methane, or mixtures thereof.) In some embodiments, curing is conducted under oxidizing conditions (e.g., under an atmosphere comprising an oxidizing gas, such as for example, oxygen, nitrous oxide, fluorine, or mixtures thereof.)

Methods of Treatment

The present invention is also directed to a method of providing an active agent to a subject, the method comprising vaginally administering a flexible, compressed intravaginal ring to the subject, wherein the flexible, compressed intravaginal ring comprises a substantially homogeneous flexible, compressed mixture comprising a polymethacrylate, a thickener, a plasticizer, and an active agent.

The terms "treat" and "treatment" refer to both therapeutic treatment and prophylactic, maintenance, or preventative measures, wherein the object is to prevent or slow down (lessen) an undesired physiological condition, disorder or disease, or obtain beneficial or desired clinical results. For purposes of this invention, beneficial or desired clinical results include, but are not limited to, alleviation of symptoms or signs; diminishment of extent of condition, disorder or disease; stabilization (i.e., not worsening) of the state of condition, disorder or disease; delay in onset or slowing of condition, disorder or disease progression; amelioration of the condition, disorder or disease state, remission (whether partial or total), whether detectable or undetectable; or enhancement or improvement of condition, disorder or disease. Treatment includes eliciting a clinically significant response, without excessive levels of side effects. Treatment also includes prolonging survival as compared to expected survival if not receiving treatment.

The present invention is also directed to a method of site specific drug delivery to the vaginal and/or urogenital tract, and the treatment of any disease in which the active agent can be absorbed in the vaginal and/or urogenital tract.

In some embodiments, a flexible, compressed intravaginal ring of the present invention can be administered to a subject to treat a menopausal condition. As used herein, a "menopausal condition" refers to a condition associated with menopause, or the period of natural cessation of menstruation. Additionally, the term "menopausal condition" can relate to a condition related to peri-menopause, post-menopause, or oophorectomized women, or women whose endogenous sex hormone production has been suppressed by a pharmaceutical chemical composition, e.g., a GnRH agonist such as leuprolide-acetate sold under the trademark LUPRONE® (TAP Pharmaceutical Products, Inc., Lake Forest, Ill.) or goserelin acetate, sold under the trademark ZOLADEX® (AstraZeneca Pharmaceuticals, Wilmington, Del.).

Various menopausal conditions can exist. In some embodiments, the menopausal condition is hot flashes. In some embodiments, the menopausal condition can be, but is not limited to, vaginal dryness, pain during intercourse, increased risk of infection, inability to control urination (e.g., incontinence), increased frequency of urinary infection, vaginal atrophy, kraurosis vulvae, hot flashes and/or night sweats, fatigue, emotional changes (e.g., mood swings and changes in sexual interest), sleep disturbances (e.g., insomnia), dry skin and hair, increased growth of facial and body hair, increased risk of heart disease, aches and pains in the joints, headaches, palpitations (i.e., rapid, irregular heart beats), vaginal itching, osteoporosis, osteopenia, and generalized itching.

In some embodiments, a flexible, compressed intravaginal ring of the present invention can be administered to a subject to treat osteoporosis. As used herein, "osteoporosis" refers to a condition characterized by a decrease in bone mass and density, causing bones to become fragile. In some embodiments, osteoporotic conditions include increased risk of fracture, especially fractures of the hip or spine.

In some embodiments, a flexible, compressed intravaginal ring of the present invention can be administered to a subject to treat incontinence. As used herein, "incontinence" refers to an inability to control urination.

In some embodiments, a flexible, compressed intravaginal ring of the present invention can be administered to a subject to treat vaginal infection. As used herein, "vaginal infection" refers to a bacterial or viral infection in or around the vagina, cervix, or uterus. Symptoms of vaginal infection include, but are not limited to, itching, burning, soreness, pain during intercourse and/or urination, and can be accompanied by vaginal discharge.

In some embodiments, a flexible, compressed intravaginal ring of the present invention can be administered to a subject to treat vaginal pain. As used herein, "vaginal pain" refers to pain localized in the female reproductive tract (e.g., the vagina, cervix, or uterus, and combinations thereof). The pain can be due to a medical condition and/or psychological difficulties. Medical conditions can include chronic diseases, minor ailments, and medications. Psychological causes can be related to physical or sexual abuse. As used herein, "abdominal pain" refers to pain in the region of the stomach, small intestine, large intestine, or bowel.

In some embodiments, a flexible, compressed intravaginal ring of the present invention can be administered to a subject to treat inflammation. As used herein, "inflammation" refers to the body's natural response to injury or infection, in which the site of injury or infection might display various degrees of pain, swelling, heat, redness and/or loss of function.

Therapeutic Kits

The present invention is also directed to a therapeutic kit comprising a flexible, compressed intravaginal ring of the present invention, and instructions for administering the flexible, compressed intravaginal ring to a female subject in need thereof.

"Instructions" for administering the flexible, compressed intravaginal ring can comprise printed matter, a pre-recorded media device, or a planner describing the use and/or proper administering of the flexible, compressed intravaginal ring to treat or prevent a condition that could be aided by intravaginal delivery of an active agent.

"Printed matter" can be, for example, one of a book, booklet, brochure or leaflet. The printed matter can describe the use of a flexible, compressed intravaginal ring of the present invention to treat a condition or disease. Possible formats include, but are not limited to, a bullet point list, a list of frequently asked questions (FAQ's), or a chart. Additionally, the information to be imparted can be illustrated in non-textual terms, e.g., using pictures, graphics or other symbols.

A "pre-recorded media device" can be, for example, a visual media device, such as a videotape cassette, a DVD (digital video disk), filmstrip, 35 mm movie or any other visual media device. Alternatively, a pre-recorded media device can be an interactive software application, such as a CD-ROM (compact disk-read only memory) or floppy disk. Alternatively, a pre-recorded media device can be, for example, an audio media device, such as a record, audiocassette, or audio compact disc. Alternatively, the pre-recorded media can be located at a publicly accessible website, or at a website that is accessible using a password distributed by a relevant person for distributing such information, and wherein the printed matter accompanying the pharmaceutical package can provide instructions for accessing the website as well as the Uniform Resource Locator ("URL") for the website, which is the address of a resource on the Internet. The information contained on a pre-recorded media device can describe the use of the flexible, compressed intravaginal rings of the present invention to treat a condition or disease.

A "planner" can be, for example, a weekly, a monthly, a multi-monthly, a yearly, or a multi-yearly planner. In some embodiments, a planner can be useful in a clinical or diagnostic setting as a diary to monitor dosage amounts or keep track of dosages administered. Alternatively, a planner can be used to prepare for future events wherein administering or removing a flexible, compressed intravaginal ring can be difficult. Alternatively, a planner can be a calendar useful for providing a means to monitor when a flexible, compressed intravaginal ring was administered, and when it should be removed. Additionally, the planner can be useful for the elderly, or other patient groups who can be responsible for self-administering and subsequently removing a vaginal ring. One skilled in the art will appreciate the variety of planning tools that would be appropriate for use with the present invention.

The therapeutic kit can also include a container for storing or packaging the components of the kit. Suitable containers include, for example, a bag, a box, a foil packet, a blister sealed package, and any other container that would be suitable for use in the present invention. In some embodiments, the kits are designed in a manner such that they are tamper resistant or the packaging can indicate if tampering has occurred. In some embodiments, the container is large enough to accommodate each component and/or any administrative devices that can accompany the flexible, compressed intravaginal ring of the present invention. In some embodiments, it can be desirable to include a small container that can be concealed in a patient's pocketbook, briefcase or pocket.

In some embodiments, the therapeutic kit of the present invention can contain one or more flexible, compressed intravaginal rings of the present invention in combination with a second pharmaceutical composition or dosage device.

In some embodiments, a therapeutic kit of the present invention contains a label, notice, or printed instructions. Such printed instructions can be in a form prescribed by a governmental agency regulating the manufacture, use, or sale of pharmaceuticals or biological products, which notice reflects approval by the agency for the manufacture, use, or sale of the flexible, compressed intravaginal rings for administration to a female human to treat a condition suitable for treatment by intravaginal delivery of an active agent.

In some embodiments, the present invention provides a method of delivering a flexible, compressed intravaginal ring of the present invention, to a patient in need thereof, the method comprising:

registering in a computer readable storage medium the identity of a physician permitted to prescribe the flexible, compressed intravaginal ring;

providing the patient with counseling information concerning a risk attendant to administering a flexible, compressed intravaginal ring;

obtaining informed consent of the patient to receive the flexible, compressed intravaginal ring despite the risk;

registering the patient in the computer readable medium after obtaining the informed consent; and permitting the patient access to the flexible, compressed intravaginal ring.

In some embodiments of this method, the access to the flexible, compressed intravaginal ring is a prescription.

The present invention is also directed to a method of educating a consumer regarding the flexible, compressed intravaginal rings of the present invention, the method comprising distributing the flexible, compressed intravaginal ring to a consumer with consumer information at a point of sale.

In some embodiments, the consumer information is presented in a format selected from the group consisting of: English language text, a foreign language text, a visual image, a chart, a telephone recording, a website, and access to a live customer service representative. In some embodiments, the consumer information is a direction for use, appropriate age use, indication, contraindication, appropriate dosing, warning, telephone number or website address.

In some embodiments, the method of educating the consumer further comprises providing professional information to a relevant person in a position to answer a consumer question regarding the flexible, compressed intravaginal ring of the present invention, or the use thereof to treat a condition. The relevant person can be a physician, physician's assistant, nurse practitioner, pharmacist, pharmacokineticist, or customer service representative.

In some embodiments, the distributing is to a location with a pharmacist or a health care provider.

All of the various embodiments or options described herein can be combined in any and all variations.

Having generally described this invention, a further understanding can be obtained by reference to the example provided herein. This example is for the purpose of illustration only and is not intended to be limiting.

EXAMPLES

Example 1

A placebo intravaginal ring (a ring containing no active agent) was prepared by the method of the present invention. The ingredients and their amounts are listed in Table 1.

TABLE 1

| Ingredient | Function | mg/vaginal ring |
|---|---|---|
| Poly(n-butyl)methacrylate | Polymer | 4500 |
| Dibutyl Sebacate | Plasticizer | 1000 |
| CAB-O-SIL ® | Thickener | 450 |
| Magnesium Stearate | Lubricant | 50 |
| Active Agent | n/a | n/a |
| Total Weight (mg) | | 6000 |

Figure 9:
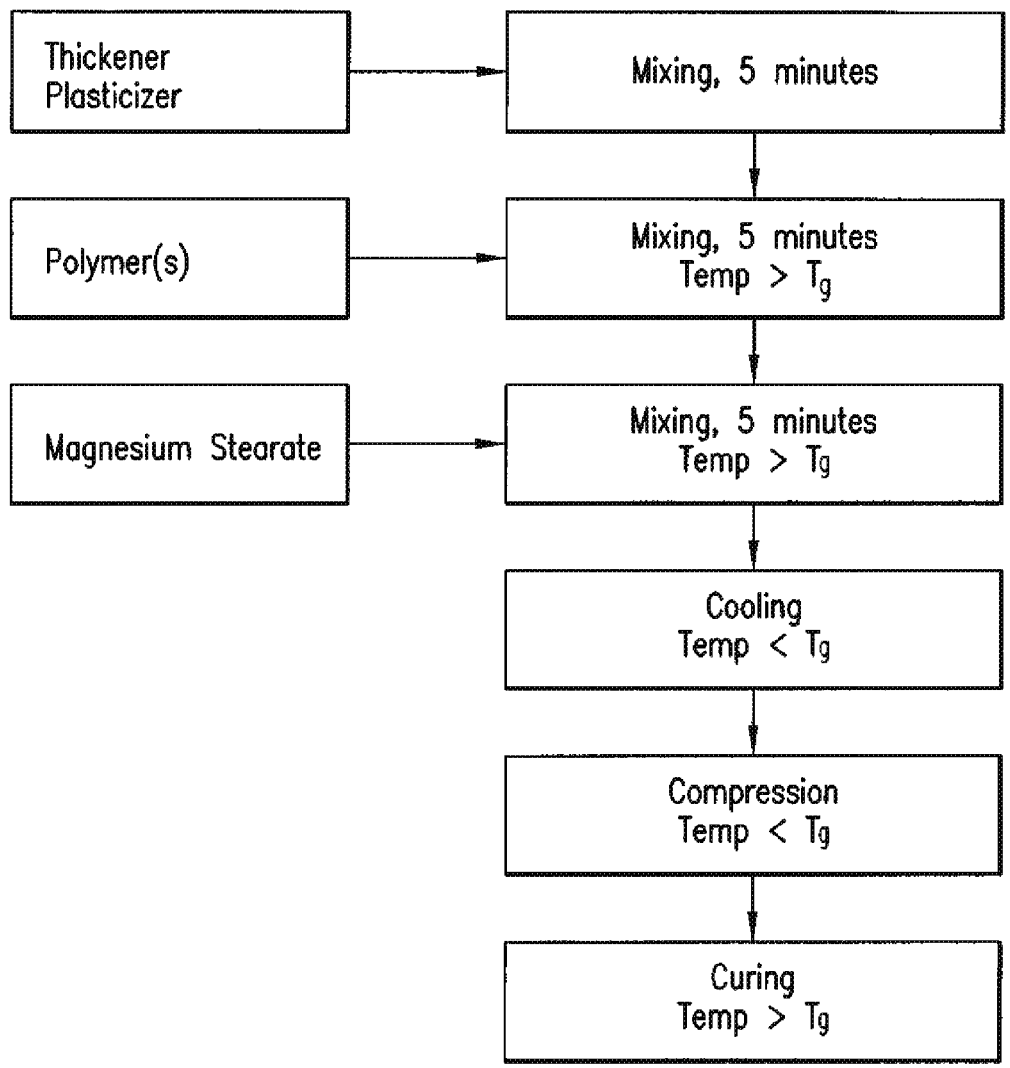
FIG. 9 is a process flow chart representing a process of mixing, compressing and curing a flexible, compressed intravaginal ring of the present invention.
Figure 10:
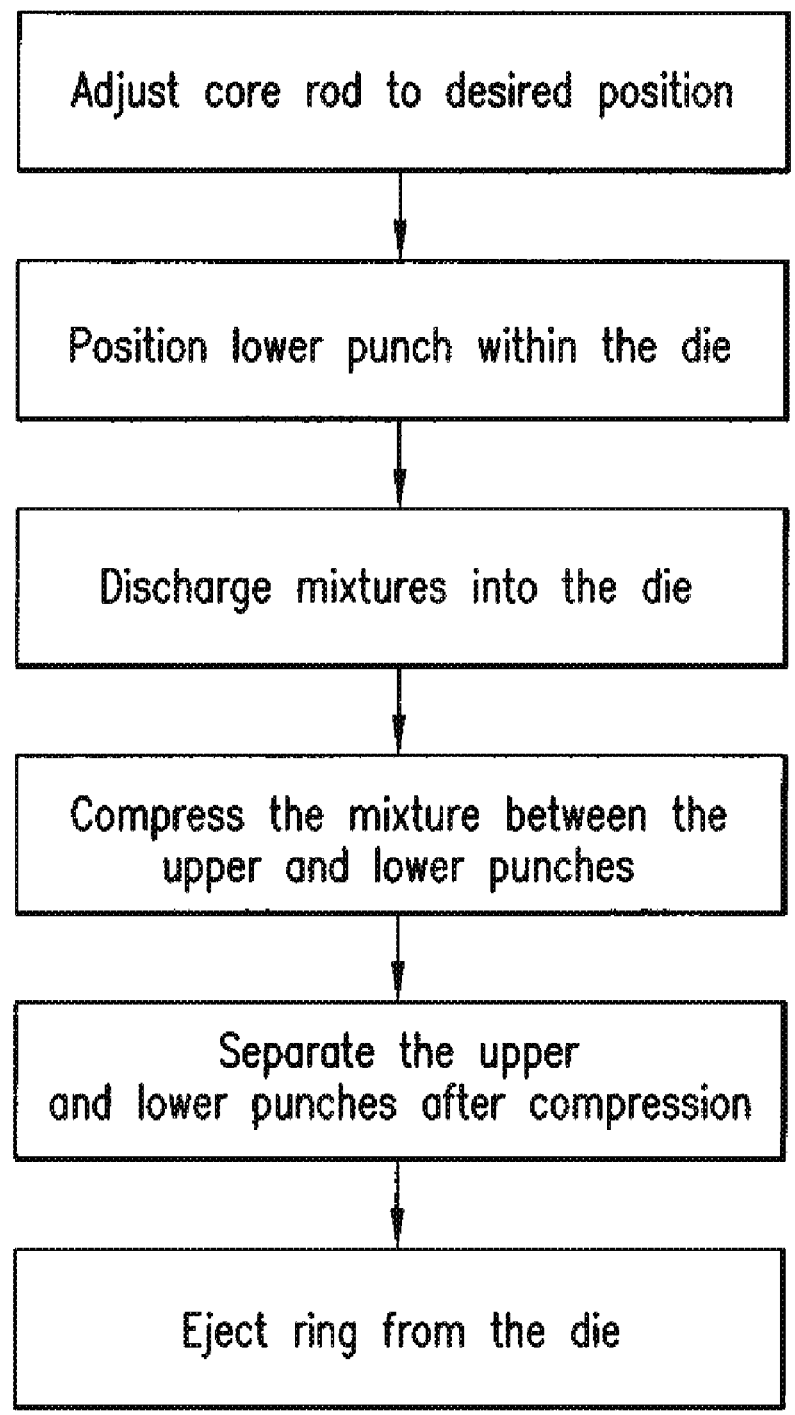
FIG. 10 is a process flow chart representing the process of compressing a mixture to form a flexible, compressed intravaginal ring of the present invention.

The process for preparing the flexible, compressed intravaginal ring is generally outlined in FIG. 9 and FIG. 10. A thickener (CAB-O-SIL®) and plasticizer (dibutyl sebacate) were mixed at room temperature (approximately 23° C.) for 5 minutes to form a first mixture. A polymer (poly(n-butyl) methacrylate having a $T_g$ of 20° C.), and then magnesium stearate, were added to the first mixture, and the resulting mixture was mixed for 5 minutes after each addition to form a homogeneous mixture. The homogeneous mixture was then cooled to 4° C. The cooled homogeneous mixture was then placed in a lower punch, depicted in FIG. 3, which was placed in a CARVER® Laboratory Press. An upper punch, core rod, die and ejector die, as described in FIG. 2 and FIGS. 4-6, respectively, were used to compress the homogeneous mixture to form a flexible, compressed intravaginal ring. During the compression process approximately 3000 pounds of pressure were applied to the mixture for a period of approximately 5 seconds. The resulting flexible, compressed intravaginal ring was then cured at 35° C. for 12 hours.

This example illustrates possible embodiments of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A flexible, compressed intravaginal ring comprising a substantially homogeneous compressed mixture comprising a polymethacrylate, a plasticizer, a thickener, and an active agent, wherein the mixture has a glass transition temperature of not greater than 80° C., and wherein the percent elongation of the intravaginal ring under a stress of about 0.5 mPa for about 5 minutes is about 30% to about 200%.

2. The flexible, compressed intravaginal ring of claim 1, wherein the polymethacrylate is selected from the group consisting of: poly(n-butyl) methacrylate, poly(isopropyl)methacrylate, poly(ethyl)methacrylate, poly(butyl) methacrylate, poly(propyl)methacrylate, poly(hexyl)methacrylate, and combinations thereof.

3. The flexible, compressed intravaginal ring of claim 1, wherein the plasticizer is selected from the group consisting of: dibutyl sebacate, triethyl citrate, castor oil, triacetin, propylene glycol, polyethylene glycol, hydrogenated vegetable oil, cetyl alcohol, cetylstearyl alcohol, fatty acids, glycerides and triglycerides, polyoxyethylene glycols, butyl lactate, ethyl glycolate, ethyl lactate, sorbitol lactate, 1,2-butylene glycol, block polymers, and combinations thereof.

4. The flexible, compressed intravaginal ring of claim 1, wherein the polymethacrylate and the plasticizer are present in a ratio of about 1:1 to about 9:1 by weight.

5. The flexible, compressed intravaginal ring of claim 4, wherein the polymethacrylate and the plasticizer are present in a ratio of about 2:1 to about 7:1 by weight.

6. The flexible, compressed intravaginal ring of claim 4, wherein the polymethacrylate and the plasticizer are present in a ratio of about 3:1 to about 6:1 by weight.

7. The flexible, compressed intravaginal ring of claim 4, wherein the polymethacrylate and the plasticizer are present in a ratio of about 3:1 to about 5:1 by weight.

8. The flexible, compressed intravaginal ring of claim 4, wherein the polymethacrylate and the plasticizer are present in a ratio of about 4:1 by weight.

9. The flexible, compressed intravaginal ring of claim 1, wherein the thickener is selected from the group consisting of: fumed silica, colloidal silica, calcium silicate, gelatinized starch, microcrystalline cellulose, talc, magnesium stearate, and combinations thereof.

10. The flexible, compressed intravaginal ring of claim 1, wherein the active agent is selected from the group consisting of: a prostaglandin, a urinary incontinence agent, an analgesic, an anti-inflammatory agent, a hormonal agent, an anti-microbial, an anesthetic, an anti-osteoporosis agent, a peptide hormone, an enzyme, and combinations thereof.

11. The flexible, compressed intravaginal ring of claim 1, further comprising a pharmaceutically acceptable excipient selected from the group consisting of a diluent, a binder, a lubricant, an antioxidant, and combinations thereof.

12. A method of providing an active agent to a subject, the method comprising vaginally administering a flexible, compressed intravaginal ring to the subject, wherein the flexible, compressed intravaginal ring comprises a substantially homogeneous compressed mixture comprising a polymethacrylate, a plasticizer, a thickener, and an active agent wherein the mixture has a glass transition temperature of not greater than 80° C. and wherein the percent elongation of the intravaginal ring under a stress of about 0.5 mPa for about 5 minutes is about 30% to about 200%.

13. A therapeutic kit comprising: (a) the flexible, compressed intravaginal ring of claim 1; and (b) instructions for administering the flexible, compressed intravaginal ring to a female subject.

14. A process for preparing a flexible, compressed intravaginal ring, the process comprising: mixing a polymethacrylate having a glass transition temperature, a plasticizer, a thickener, and an active agent at a temperature above the glass transition temperature of the polymethacrylate to form a substantially homogeneous mixture; and compressing the substantially homogeneous mixture at a temperature below the glass transition temperature of the mixture to form a flexible, compressed intravaginal ring wherein the mixture has a glass transition temperature of not greater than 80° C., and wherein the percent elongation of the intravaginal ring under a stress of about 0.5 mPa for about 5 minutes is about 30% to about 200%.

15. The process of claim 14, further comprising cooling the substantially homogeneous mixture to a temperature below the glass transition temperature of the mixture.

16. The process of claim 14, further comprising curing the flexible, compressed intravaginal ring.

17. The process of claim 14, wherein curing comprises heating the flexible, compressed intravaginal ring to a temperature above the glass transition temperature of the mixture.

18. The process of claims 14, wherein the polymethacrylate has a glass transition temperature of about 10° C. to about 50° C.

19. The process of claim 14, wherein the polymethacrylate is selected from the group consisting of: poly(n-butyl)methacrylate, poly(isopropyl) methacrylate, poly(ethyl)methacrylate, poly(butyl)methacrylate, poly(propyl) methacrylate, poly(hexyl)methacrylate, and combinations thereof.

20. The process of claim 14, wherein the plasticizer is selected from the group consisting of dibutyl sebacate, triethyl citrate, castor oil, triacetin, propylene glycol, polyethylene glycol, hydrogenated vegetable oil, cetyl alcohol, cetylstearyl alcohol, fatty acids, glycerides and triglycerides, polyoxyethylene glycols, butyl lactate, ethyl glycolate, ethyl lactate, sorbitol lactate, 1,2-butylene glycol, block polymers, and mixtures thereof.

21. The process of claim 14, wherein the thickener is selected from the group consisting of: fumed silica, colloidal silica, calcium silicate, gelatinized starch, microcrystalline cellulose, talc, magnesium stearate, and combinations thereof.

22. The process of claim 14, wherein the active agent is selected from the group consisting of: a prostaglandin, a urinary incontinence agent, an analgesic, an anti-inflammatory agent, a hormonal agent, an anti-microbial, an anesthetic, an anti-osteoporosis agent, a peptide hormone, an enzyme, and combinations thereof.

23. The process of claim 14, wherein the compressing comprises: providing a compression tooling apparatus comprising a die, an upper punch, a lower punch and a core rod; discharging the substantially homogeneous mixture into the die; compressing the mixture between the upper punch and the lower punch to form the flexible, compressed intravaginal ring; separating the upper and lower punches after compressing; and ejecting the flexible, compressed intravaginal ring from the die.

24. The process of claim 22, wherein the lower punch has a cylindrical bore and the core rod is inserted in the cylindrical bore and adjusted to a desired position.

25. The process of claim 23, wherein the cylindrical bore and the core rod have threads for adjusting the core rod to a desired position.

26. The process of claim 24, wherein the upper punch has a cavity and during the compression the core rod enters into the cavity of the upper punch.

27. The process of claim 25, wherein the die has a cavity and a diameter of the cavity controls a size of an outer diameter of the flexible, compressed intravaginal ring.

28. The process of claim 26, wherein the core rod has a diameter and the diameter of the core rod controls a size of an inner diameter of the flexible, compressed intravaginal ring.

29. A product prepared by the process of claim 14.

* * * * *